United States Patent [19]
Homan

[11] Patent Number: 5,968,963
[45] Date of Patent: Oct. 19, 1999

[54] PLA₂ INHIBITORS AND THEIR USE FOR INHIBITION OF INTESTINAL CHOLESTEROL ABSORPTION

[75] Inventor: Reynold Homan, Ann Arbor, Mich.

[73] Assignee: Warner-Lambert Company, Morris Plains, N.J.

[21] Appl. No.: 08/610,030

[22] Filed: Mar. 4, 1996

Related U.S. Application Data

[60] Division of application No. 08/450,660, May 30, 1995, Pat. No. 5,578,639, which is a continuation-in-part of application No. 08/269,746, Jul. 1, 1994, Pat. No. 5,504,073.

[51] Int. Cl.⁶ .......................... A61K 31/41; C07D 257/06
[52] U.S. Cl. .......................... 514/381; 548/251; 548/557; 548/577; 560/205; 564/104; 564/106; 564/204; 564/209; 570/127; 570/184
[58] Field of Search .................. 548/251, 557, 548/577; 564/204, 106, 104, 209; 560/205; 570/127, 184; 514/381

[56] References Cited

U.S. PATENT DOCUMENTS

| | | | |
|---|---|---|---|
| 3,573,290 | 3/1971 | Sallmann et al. | 260/240 |
| 4,161,529 | 7/1979 | Beregi et al. | 424/274 |

FOREIGN PATENT DOCUMENTS

| | | |
|---|---|---|
| 0263229 | 4/1988 | European Pat. Off. . |
| 0360685 | 3/1990 | European Pat. Off. . |
| 0377896 | 7/1990 | European Pat. Off. . |
| 0401857 | 12/1990 | European Pat. Off. . |
| 9012004 | 10/1990 | WIPO . |
| 9418167 | 8/1994 | WIPO . |

OTHER PUBLICATIONS

"Alkylation Studies with Aminotetrazoles", K. Wilson, R. Herbst and Willard Haak, *J. Org. Chem.*, 24 (1046–51); 1959.

"Synthesis of Iminotetrazoline Derivatives as Trichomonacidal and Fungicidal Agents," Robert Herbst and Charles F. Froberger, *J. Org. Chem.* 22(1050–1053); 1957.

"Alkylated 5–Aminotetrazoles, Their Preparation and Properties", Douglas F. Percival and Robert M. Herbst, *J. Org. Chem.* 22 (925–33); 1957.

*J. Lipid Res.*, vol. 22, pp. 744–752 (1981), Rampone et al.

*Lipids*, vol. 15, pp. 395–400 (1980), Hollander et al.

*J. Lipid Res.*, vol. 21, pp. 525–536 (1980), Beil et al.

*Biochim. Biophys. Acta*, vol. 486, pp. 500–510 (1977), Rampone et al.

*Digestive Diseases*, vol. 23, pp. 316–320 (1978), O'Connor et al.

*J. Lipid Res.*, vol. 34, pp. 377–395 (1993), Harwood et al.

*Arch Intern Med.*, vol. 153, pp. 1345–1353 (1993), Dressman et al.

*Atherosclerosis VIII*, pp. 791–794 (1989), Kesäniemi et al.

*Biochemistry*, vol. 30, No. 42, pp. 10256–10268 (1991), Jain et al.

*J. Med. Chem.*, vol. 35, No. 19, pp. 3584–3586 (1992), Jain et al.

PCT International Search Report, PCT/US 95/08167.

Grogan, et al., *J. Pharm. Sci.*, vol. 61, No. 6, 1972, pp. 802–803.

*Primary Examiner*—Johann Richter
*Assistant Examiner*—Jane C. Osowecki
*Attorney, Agent, or Firm*—Charles W. Ashbrook

[57] ABSTRACT

Certain compounds have been synthesized and found to be effective inhibitors of phospholipase A₂ (PLA₂), and thereby useful in the treatment of intestinal cholesterol absorption and the disease states arising therefrom, such as hypercholesterolemia and coronary artery disease.

5 Claims, 17 Drawing Sheets

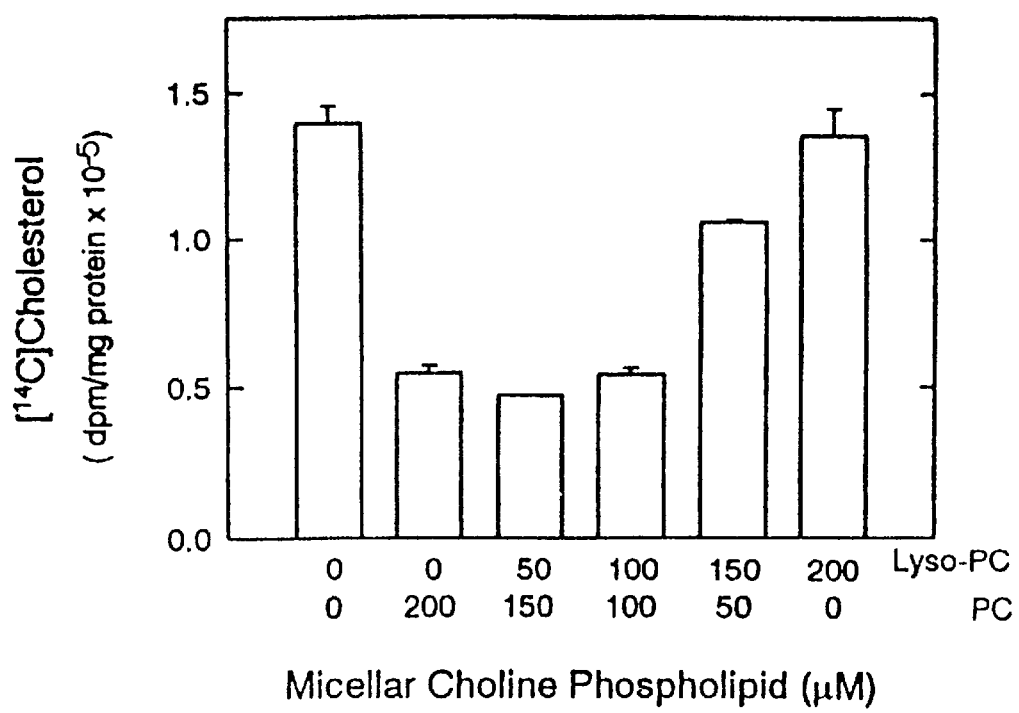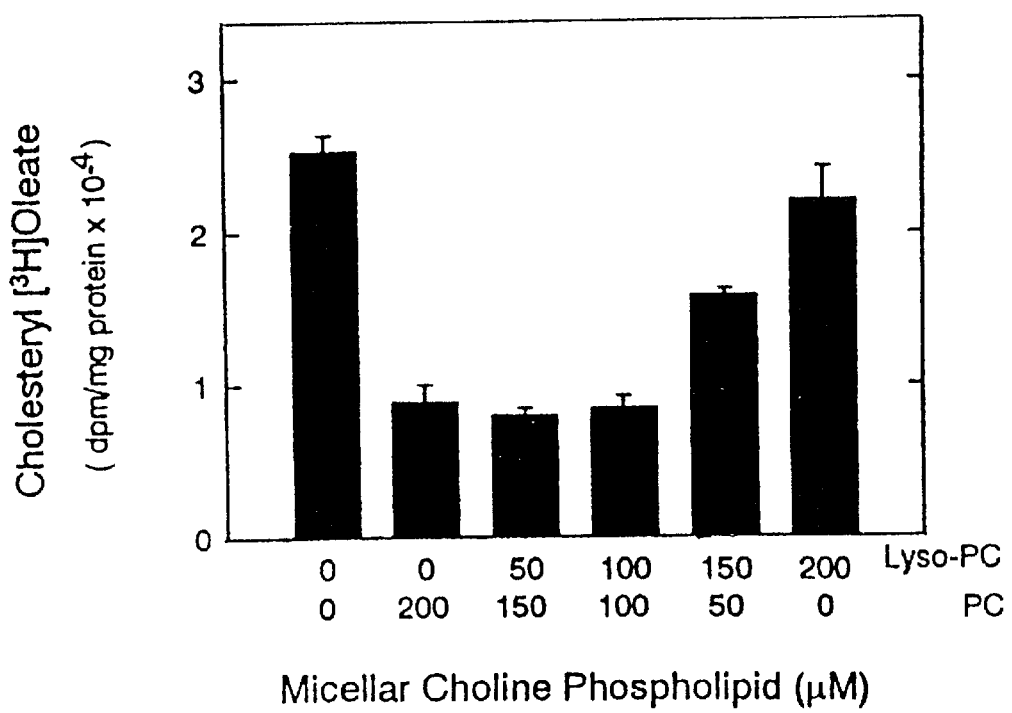

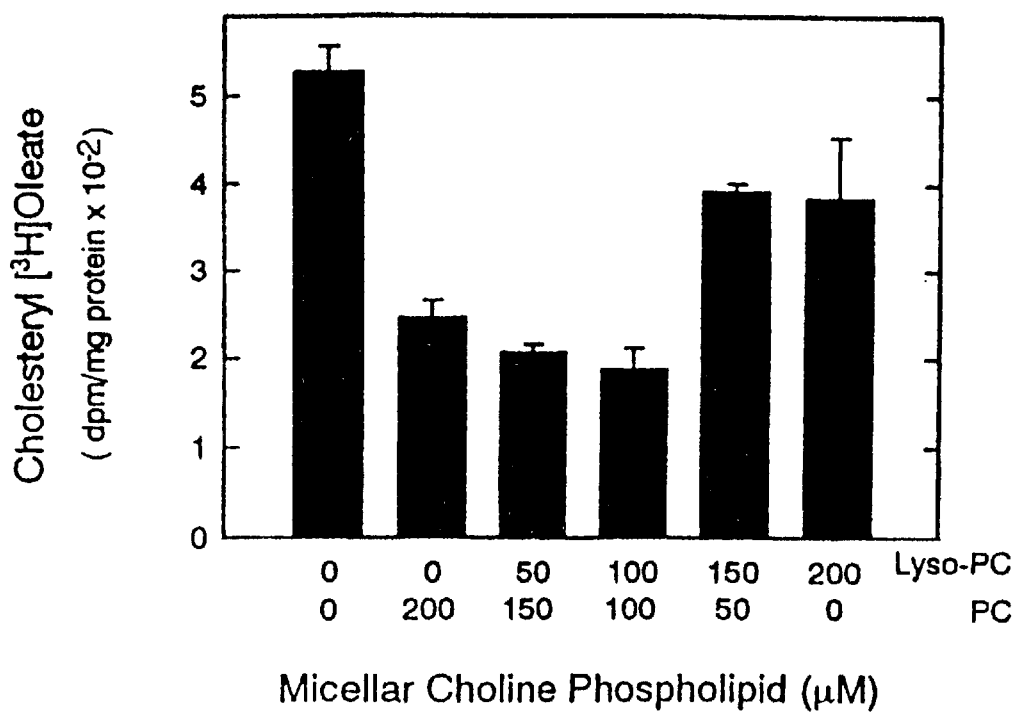
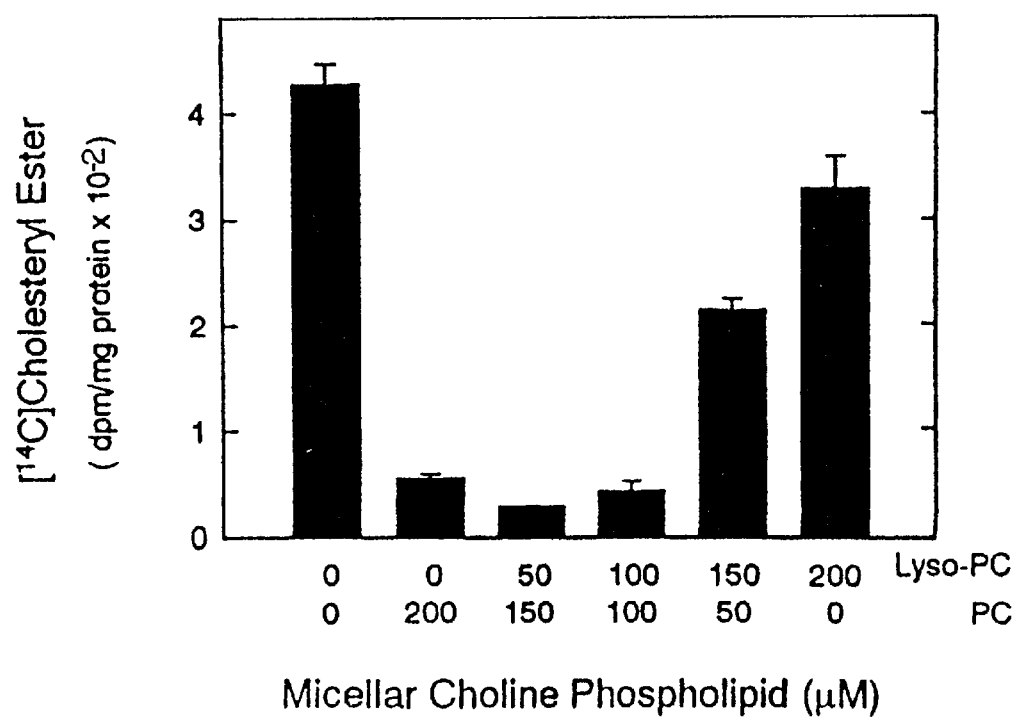

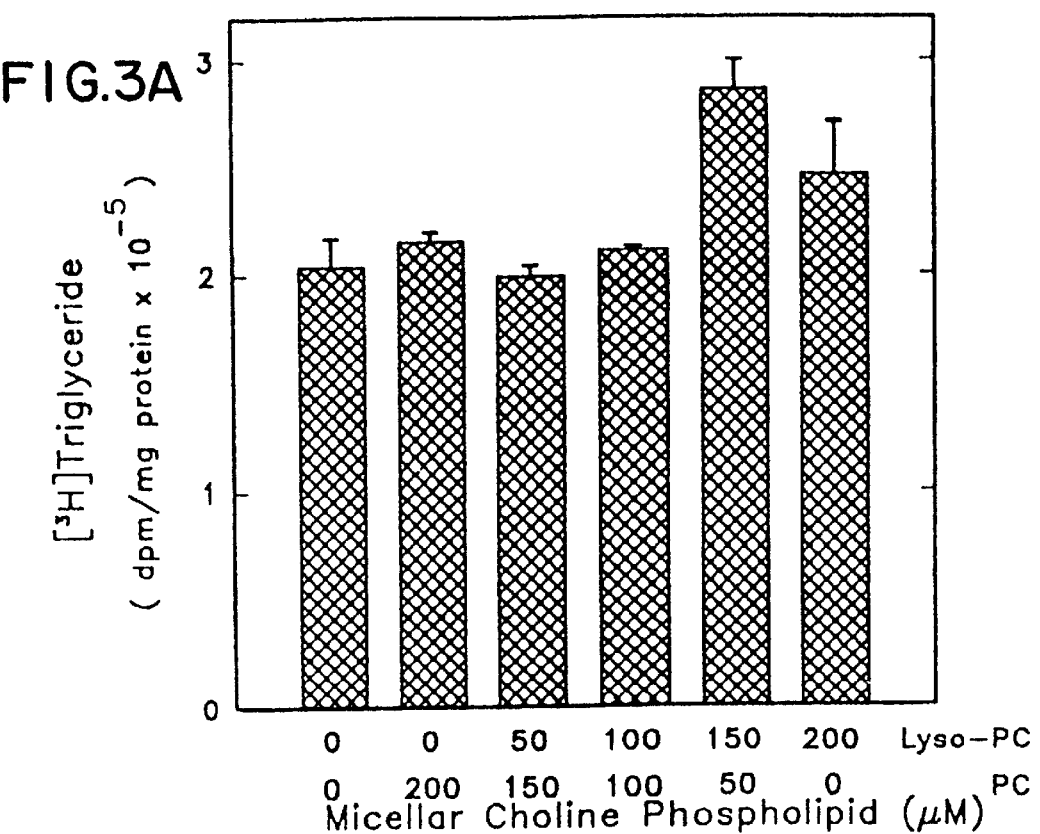
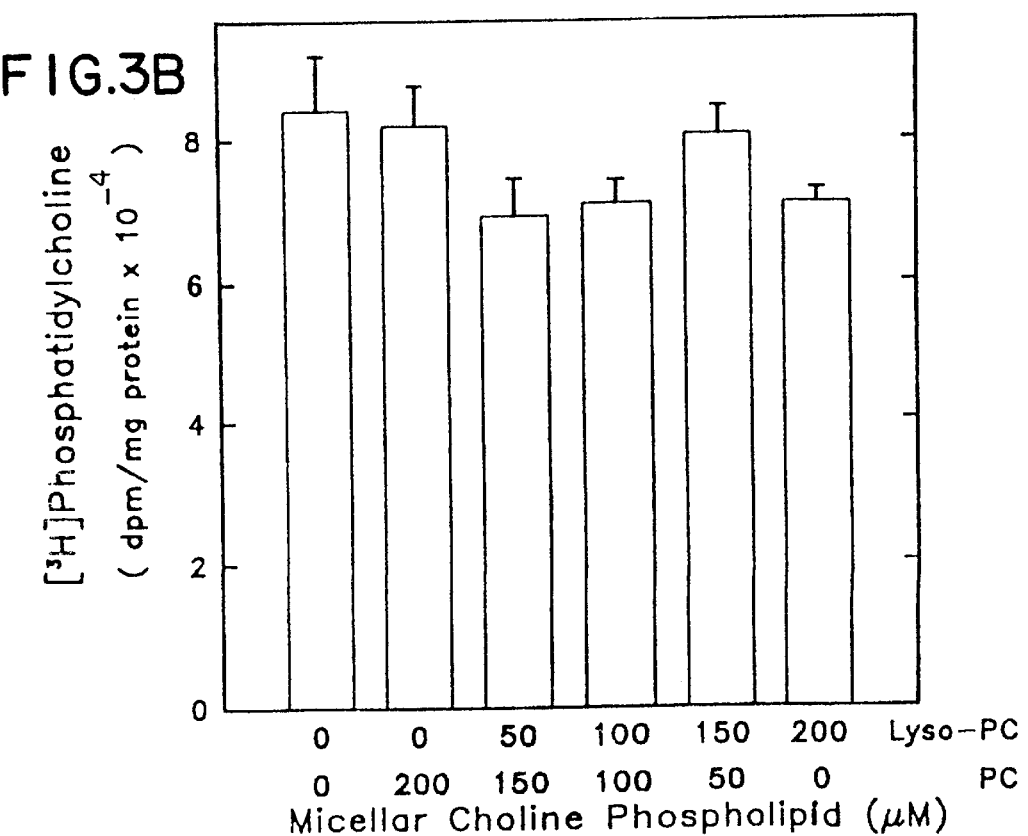

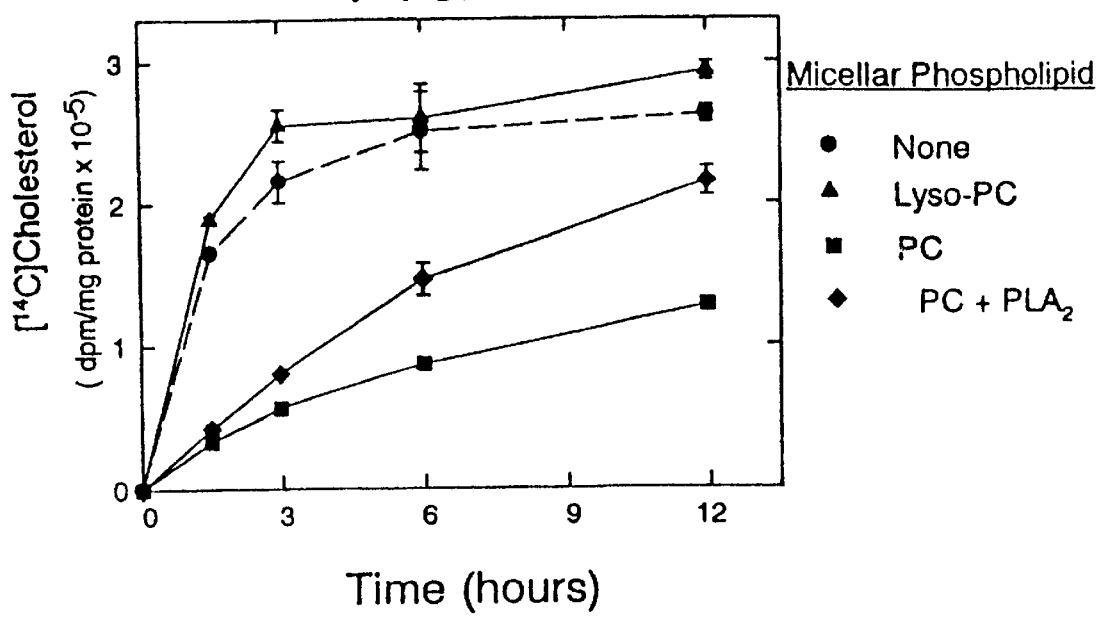
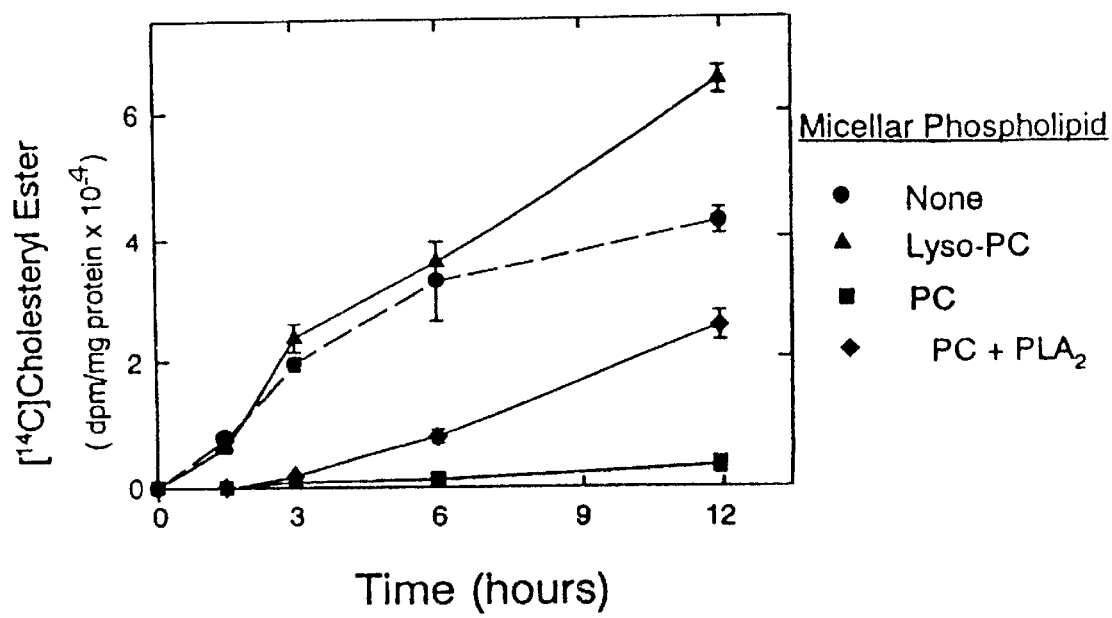

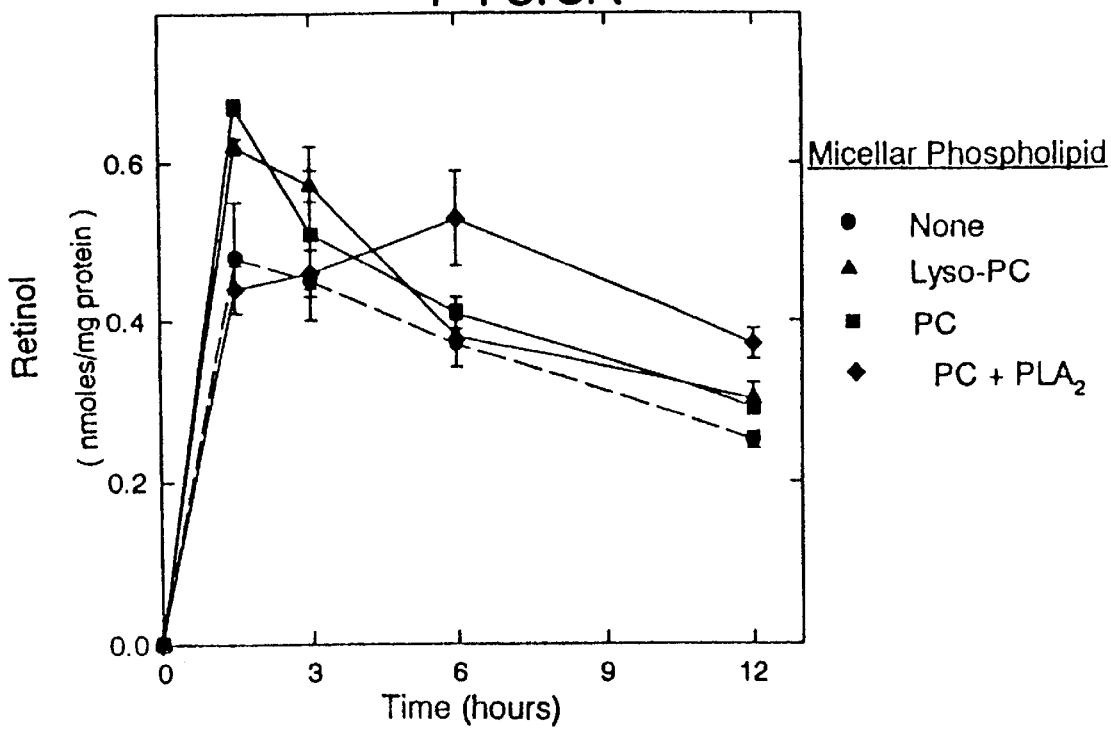
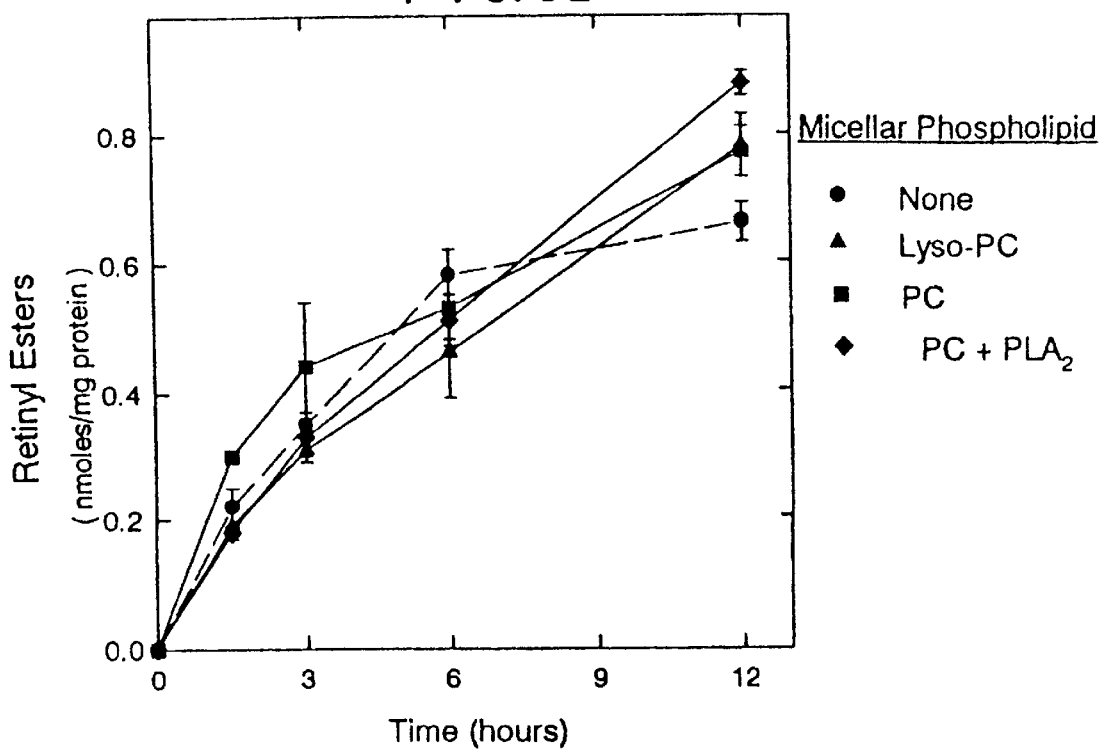

PLA₂ INHIBITORS AND THEIR USE FOR INHIBITION OF INTESTINAL CHOLESTEROL ABSORPTION

This is a division of Ser. No. 08/450,660, filed on May 30, 1995, now U.S. Pat. No. 5,578,639 which is a CIP of Ser. No. 08/269,746, filed on Jul. 1, 1994, now U.S. Pat. No. 5,504,073.

BACKGROUND OF THE INVENTION

Cholesterol that is absorbed from the intestinal contents contributes significantly to the plasma levels of non-HDL cholesterol. Since non-HDL cholesterol is a positive risk factor for the progression of atherosclerosis and coronary artery disease (CAD), methods to inhibit intestinal cholesterol absorption have clinical potential for the treatment of hypercholesterolemic patients at risk for CAD.

Phosphatidylcholine (hereinafter "PC"), which enters the intestinal lumen from the bile and the diet, is considered to participate in cholesterol absorption by enhancing the solubility of cholesterol in bile acid micelles. Tt has been reported, however, that biliary PC also retards intestinal cholesterol absorption. This diametric effect of PC on cholesterol absorption was confirmed in later in vitro studies with isolated rat intestinal segments (Rampone A. J. and Machida C. M., "Mode of action of lecithin in suppressing cholesterol absorption." *J. Lipid Res.*, 22:744–752 (1981)), and in intestinal perfusion studies (Hollander D., and Morgan D., "Effect of plant sterols, fatty acids and lecithin on cholesterol absorption in vivo in the rat." *Lipids*, 15:395–400 (1980)). Similar suppression of cholesterol absorption by PC has been demonstrated in vivo in human subjects (Beil F. U. and Grundy S. M., "Studies on plasma lipoproteins during absorption of exogenous lecithin in man" *J. Lipid Res.*, 21:525–536 (1980)).

Lumenal PC is hydrolyzed to lysophosphatidylcholine and free fatty acid by pancreatic phospholipase A₂. When the effect of lysophosphatidylcholine on cholesterol absorption by intestinal segments was examined no inhibition was observed indicating that intact PC is required to suppress cholesterol absorption (Rampone A. J. and Long L. R., "The effect of phosphatidylcholine and lysophosphatidylcholine on the absorption and mucosal metabolism of oleic acid and cholesterol in vitro." *Biochim. Biophys. Acta*, 486:500–510 (1977)).

The foregoing conclusion that PC in the intestinal contents blocks intestinal lipid absorption is supported by studies in which cholesterol absorption was significantly inhibited in rats fed a cholesterol-loaded lipid emulsion containing nondigestible diether PC analogs (O'Connor P. J., Loiudice T. A., Bochenek W., and Rodgers J. B., "Effect of diester and diether phosphatidylcholine on intestinal absorption of neutral and acidic sterols." *Digestive Diseases*, 23:316–320 (1978)).

The hydrolysis of PC by pancreatic phospholipase A₂ appears to be a critical step in the initiation of intestinal cholesterol absorption. The dependence of cholesterol absorption on pancreatic phospholipase A₂ activity can be the basis for pharmacological treatment of hyperlipidemic persons with nonabsorbable pancreatic phospholipase A₂ inhibitors.

SUMMARY OF THE INVENTION

The present invention relates to the administration of pancreatic phospholipase A₂ inhibitors for the purpose of preventing intestinal cholesterol absorption and thereby reducing blood cholesterol levels in hypercholesterolemic patients. The present invention also concerns the discovery of a class of novel compounds that act to inhibit the absorption of cholesterol. As inhibitors of intestinal cholesterol absorption, pancreatic phospholipase A₂ inhibitors are used to treat hypercholesterolemic patients at risk for coronary artery disease. The compounds are administered in combination with a pharmaceutically acceptable carrier in a therapeutically effective amount to a patient in need thereof.

DETAILED DESCRIPTION OF THE INVENTION

Accordingly, one embodiment of the present invention is a method for blocking intestinal cholesterol absorption in animals comprising administering an effective amount of a pancreatic phospholipase A₂ inhibitor. Another embodiment is a method for reducing blood cholesterol levels in hypercholesterolemic subjects comprising administering to a subject in need of treatment a therapeutically effective amount of a pancreatic phospholipase A₂ inhibitor.

Another embodiment of the present invention is a compound of Formulas I–II:

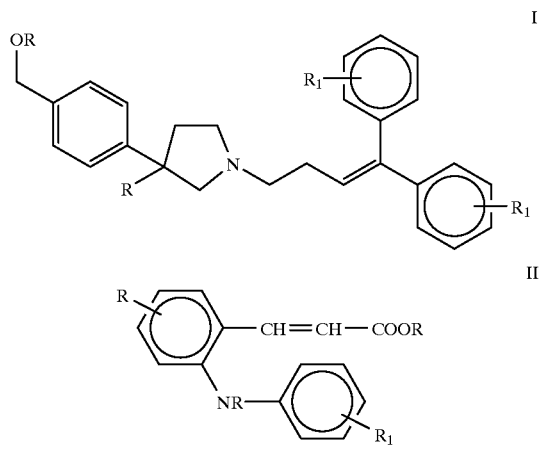

or a pharmaceutically acceptable salt thereof; wherein R and R₁ are selected from the group consisting of hydrogen, hydroxy, lower alkyl, halogen, trifluoromethyl, cyano, nitro, methylthio, lower alkenyl, and lower alkynyl.

The terms in the invention generally have the following meaning.

Lower alkyl means a straight chained or branched chain of from one to four carbon atoms including but not limited to methyl, ethyl, propyl, butyl.

Lower alkenyl means a group from 2 to 4 carbon atoms, for example, but not limited to ethylene, 1,2- or 2,3-propylene, 1,2-, 2,3-, or 3,4-butylene or isomers thereof.

Lower alkynyl means a group from two to four carbon atoms, for example, but not limited to ethynyl, 2,3-propynyl, 2,3-, or 3,4-butynyl or isomers thereof.

Lower alkoxy means a group of from one to four carbon atoms, for example, but not limited to methoxy, ethoxy, propoxy, butoxy or isomers thereof.

Halogen is fluorine, chlorine, bromine, or iodine.

Preferably, R is a lower alkyl which is most preferably a methyl group.

It is also preferable that R₁ is a halogen. Where R₁ is a halogen in Formula I, it is preferred that R₁ is a fluorine, and most preferably a fluorine substituted in the 4-position. Where R₁ is a halogen in Formula II, it is preferred that R₁ is either a chlorine or a fluorine, and most preferably a chlorine in the 3-position and a fluorine in the 2-position.

Preferably, the present invention is a compound selected from the group consisting of:

1-[4,4-bis(4-fluorophenyl)butyl]-3-(3-methoxyphenyl)-3-methyl-pyrrolidine;
2-(M-chloroanilino)-5-methyl-trans-cinnamic acid; and
2-(O-fluoroanilino)-5-methyl-trans-cinnamic acid.

Compounds of the instant invention include solvates, hydrates, and pharmaceutically acceptable salts of the compounds above.

Some of the compounds of the instant invention contain asymmetric carbon atoms. The instant invention includes the individual enantiomers, which may be prepared or isolated by methods known in the art.

Selected compounds of the present invention can exist also as syn and anti forms and are also the present invention. Selected compounds can also exist as E and Z double bond isomers. Both forms are included in the present invention.

Any resulting racemates can be resolved into the optical antipodes by known methods, for example by separation of the dastereomeric salts thereof, with an optically active acid, and liberating the optically active compound by treatment with a base. Racemic compounds of the instant invention can thus be resolved into their optical antipodes e.g., by fractional crystallization of d- or l- (tartrates, mandelates, or camphorsulfonate) salts.

Additional methods for resolving optical isomers, known to those skilled in the art may be used, for example those discussed by J. Jaques, A. Collet, and S. Wilen in "Enantiomers, Racemates and Resolutions", John Wiley and Sons, New York (1981).

Preparation of the Compounds of the Invention

The compounds of the present invention are prepared from known starting materials via various procedures, for example, methods as described below:

Compound 1

A.

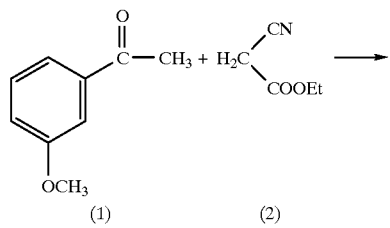

(1)  (2)

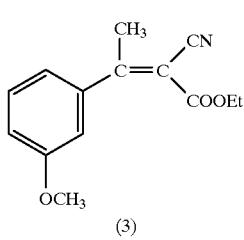

(3)

A mixture of 460 g (3.06 M) of sodium methoxy acetophenone, 700 g (6.2 M) ethyl cyano acetate, 200 mL glacial acetic acid, 50 g beta-alanine and 500 mL hexane was refluxed under a water trap for 18 hours. Added 20 g beta-alanine and continued refluxing 6 hours—essentially no water coming off stripped rotary evaporator. Added 1.5 L ether washed with 5×400 mL water then with saturated $N_2HCO_3$, diluted with HCl, dried and evaporated. Residue was distilled under reduced pressure to give 365 g (3) (48% yield), bp 135–140.

B.

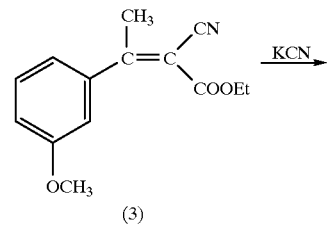

(3)

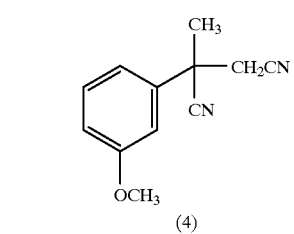

(4)

365 g of (3) (1.49 M) was dissolved in 400 mL of ethanol. Added solution of 106 g (1.68 M KCN in 150 mL water. Stirred and refluxed 18 hours. Decanted ethanol from gummy residue and stirred with a rotary evaporator. Residue dissolved in ether, washed in 3×350 mL water, dried over $MgSO_4$, filtered, and evaporated. Residue carefully distilled under reduced pressure to 237 g (4) (80%) bp 128–131.

C.

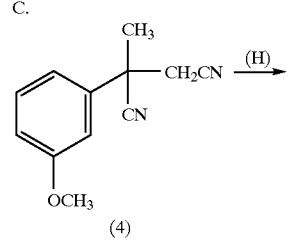

(4)

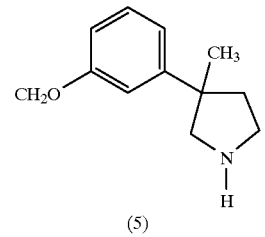

(5)

236 g of (4) reduced in methanol with concentrated $H_2SO_4$ added on Pd/c and filtered. Stripped on rotary evaporator, dissolved in ice and water, added x-5 50% NaOH and added ether. Ether solution washed with water, dried, and evaporated. Residue distilled to give 187 g (5) (83%) bp 88–90.

D.

(6)  (7)

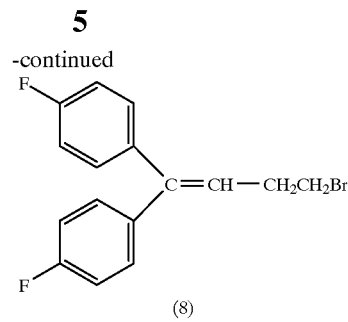

(8)

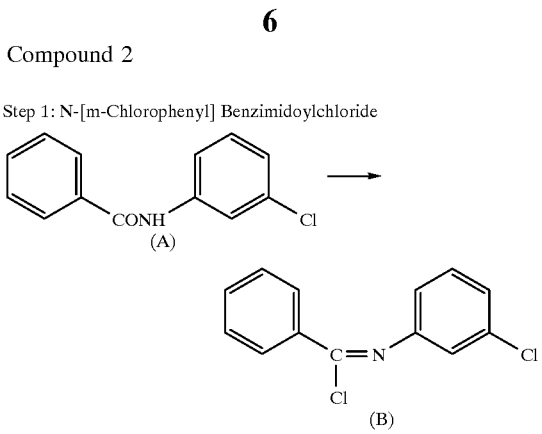

977 g (5.58 M) of bromobenzene converted to Grignard in usual manner in final solution of 5 L. Added slowly 192 g (2.23 M) of butyl alcohol in 700 mL ether. Stirred and refluxed 2 hours. Added 800 mL concentrated HBr, then 1.5 L water, stirred well, and separated. Organic layer evaporated. Residue mixed with 1500 mL 48% HBr and refluxed vigorously for 40 hours. Diluted with ice and water, extracted twice with ether. Ether layer washed with water, diluted NaOH, water, dried over MgSO$_4$, filtered, and evaporated. Residue distilled under reduced pressure to give 513 g (8) (71%), bp 129–131.

Compound (A) 23.17 g (0.1 M) and phosphorous pentachloride 20.8 g (0.1 M) are stirred together and cooled with a water bath of 20–25° C. The water bath is then slowly heated, the reaction mixture becomes liquid, and HCl evolves. The heating is continued for 20 minutes at 80° C. After being allowed to cool to room temperature, the POCl$_3$ is stripped as completely as possible, using reduced pressure. The stripping is repeated with 2×50 mL dry benzene. The residue (B) is dissolved in 100 mL dry ether. This solution in ether is directly used in Step 3.

E.

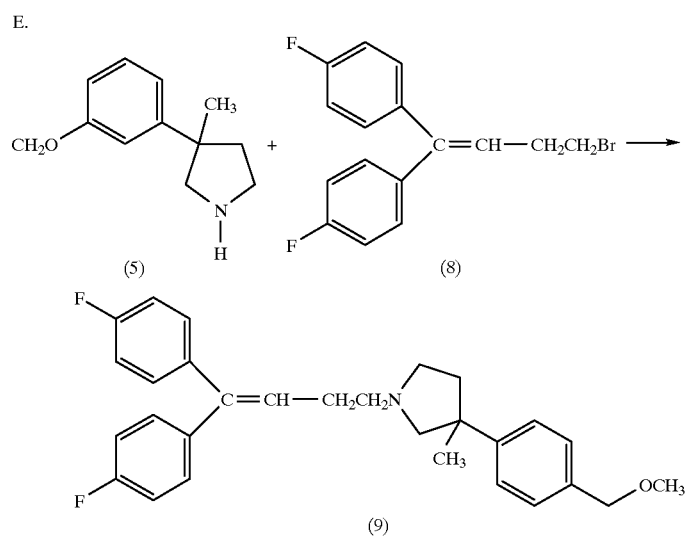

43 g (0.225 g) of (5), 76.5 g (0.237 M) (8), 50 g K$_2$CO$_3$ and 200 mL acetonitrile were stirred and refluxed for 20 hours. Filtered and stripped on rotary evaporator. Residue dissolved in ether, washed with water, dried over MgSO$_4$, filtered, and evaporated. Residue treated with 20 mL acetic anhydride, diluted with ether, and extracted with diluted HCl. Aqueous phase and oily hydrochloride removed, made basic and extracted with ether. Ether solution washed with water, dried over MgSO$_4$, filtered, and evaporated. Residue converted to hydrochloride and isopropanol/ether. Gives 50 g, mp 123–127, isopropanol/ether gives 43 g (9), mp 123–127, 10 g; toluene gives 8 g, mp 127–130;

Analysis calculated for: C, 71.55; H, 6.43; N, 2.90. Found: C 71.66; H 6.48; N 2.99

Step 2:

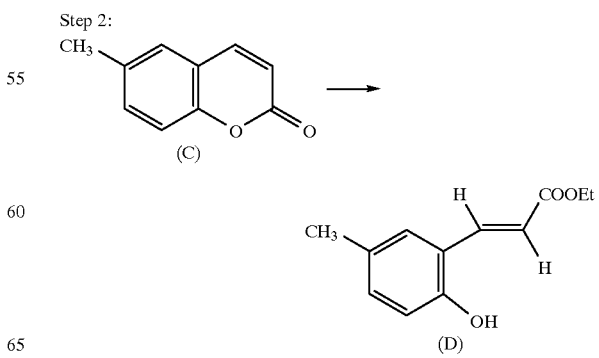

6-Methylcoumarin (C), 80 g (0.5 M), is added to a solution of 17.2 g (0.75 M) sodium in 350 mL absolute EtOH. The reaction solution is refluxed overnight (exclude moisture). After being allowed to cool to room temperature, the reaction solution is poured into 2000 mL ice water. The product is precipitated by dropwise addition of 50 mL AcOH in 300 mL water with stirring and seeding. After being cooled with an ice bath, the solid (D) is collected, washed with water, and dried in vacuo at 60° C. overnight. Yield: 94.5 g off white solid, mp 112–1140C.

Step 3: Solid (D) + Ethyl Trans-2-Hydroxy-5-Methyl-Cinnamate

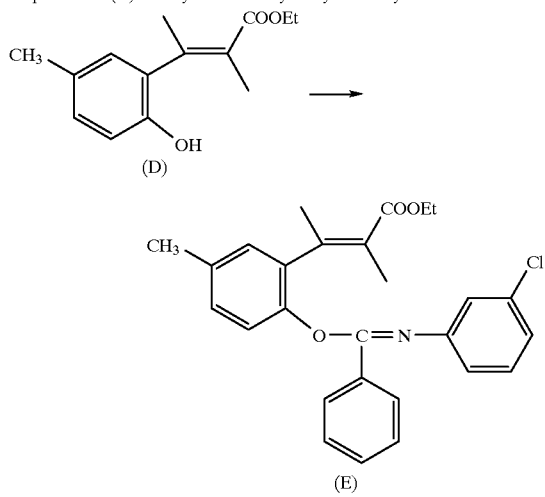

Sodium, 2.3 g (0.1 M), is dissolved in 100 mL dry ethanol. The solution is stirred and cooled with an ice bath. Solid (D), 20.6 g (0.1 M), in 50 mL dry THF is added in portions, followed by a dropwise addition of the solution of residue (B) (during 30 minutes), maintaining a temperature of 0–5° C. The stirring is continued at room temperature overnight. The reaction mixture is then poured into 1000 mL cold water, extracted with 3×150 mL benzene. The combined extracts are washed with water, dried over MgSO$_4$, the benzene is stripped at reduced pressure, leaving 42 g of pale yellow syrup. This crude product (E) is directly used in Step 4.

Step 4: Trans-2-[m-chloroanilino]-5-methylcinnamic acid

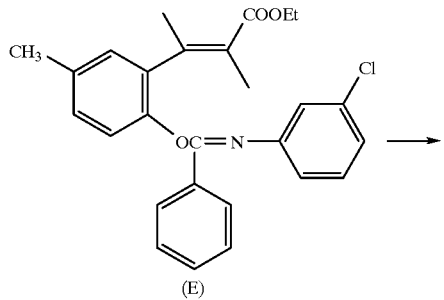

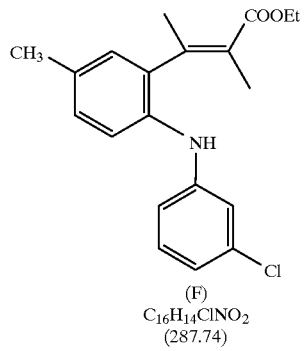

(F)
C$_{16}$H$_{14}$ClNO$_2$
(287.74)

Product (E) is heated to 300° C. using a metal bath. The temperature is measured inside the reaction mixture. After being allowed to cool to room temperature, the reaction mixture is taken up in 350 mL ethanol, 50 mL 50% NaOH and 50 mL water is added and the solution refluxed on a steam bath for 3 hours. The bulk of EtOH is stripped at reduced pressure, the residue taken up in 1000 mL warm water. The product is precipitated with a mixture of 100 mL concentrated HCl acid and 200 mL water at once. The oily precipitate solidifies upon standing. The solid is collected, washed with water, triturated with 80 mL CCl$_4$, and washed with water and CCl$_4$. The yellow solid is recrystallized, washed, and dried in vacuo at 100° C. for 3 hours. Yield: 7.6 g bright yellow solid (F), mp 166–168° C.

Sample: Recrystallized from 50% EtOH, mp 167–168° C. Calculated: C, 66.80%; H, 4.91%; N, 4.87%; Cl, 12.33%. Found: C, 66.82%; H, 4.96%; N, 4.91%. Compound 3

Step 1:

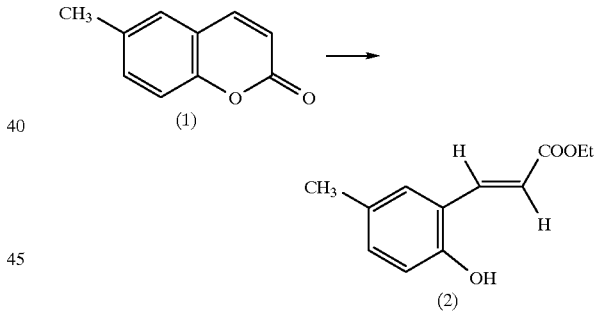

6-Methylcoumarin (1), 80 g (0.5 M), is added to a solution of 17.2 g (0.75 M) sodium in 350 mL absolute EtOH. The reaction solution is refluxed overnight (exclude moisture). After being allowed to cool, the reaction solution is poured into 2000 mL ice water. The product is precipitated by dropwise addition of 50 mL AcOH in 300 mL water with stirring and seeding, cooled with an ice bath, the solid (2) is collected, washed with water, and dried in vacuo at 60° C. overnight. Yield: 94.5 g off white solid, mp 112–114° C.

Step 2: N- benzoyl-o-fluoroaniline

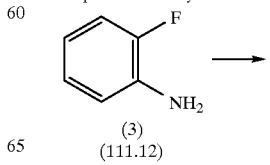

(3)
(111.12)

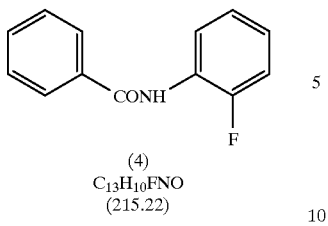

(4)
C₁₃H₁₀FNO
(215.22)

A solution of 50 g (0.45 mol) of o-fluoroaniline (3) and 450 mL of benzene is stirred and heated. Next, 57.5 mL (0.5 M) benzoylchloride is added dropwise. The reaction mixture is refluxed overnight. HCl evolves and the precipitated HCl salt disappears gradually, a clear solution results. After being allowed to cool to room temperature, the same volume of hexane is added, and the flask is scratched with a glass rod, whereupon crystallization occurs. The solid (4) is collected, washed with hexane, and dried in vacuo at 60° C. overnight. Yield: 81.5 g nearly white solid, mp 111–113° C.

Step 3: N-[o-Fluorophenyl] benzimidoylchloride

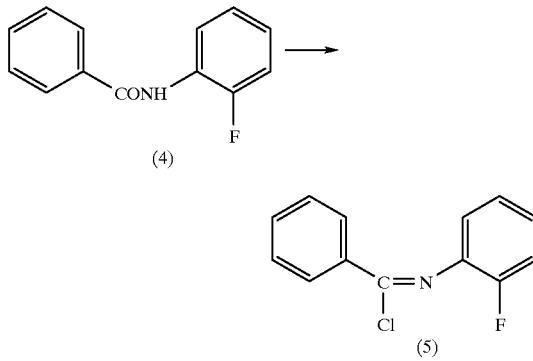

Compound (4) 21.5 g (0.1 M) and PCl₅ 20.8 g (0.1 M) are stirred together and cooled with a water bath of 20–25° C. The water bath is then heated to 80° C., and the solid mixture liquifies under HCl gas evolution. The stirring is continued at 80° C. for 20 minutes. The POCl₃ is stripped at reduced pressure, the stripping repeated with 2×50 mL dry benzene. The residue (5) is dissolved in 100 mL dry ether and directly used in Step 5 (eventually filtered).

Step 4:

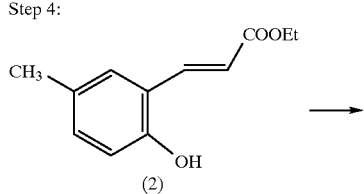

(2)

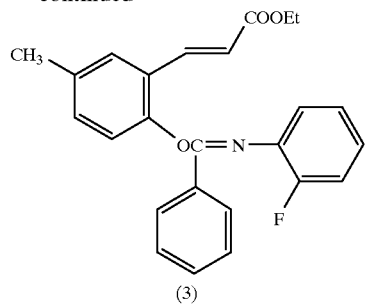

(3)

Sodium, 2.3 g (0.1 M), is dissolved in 100 mL absolute EtOH. The solution is stirred and cooled with an ice bath. Compound 2, 20.6 g (0.1 M), in 50 mL dry THF is added in portions, followed by a dropwise addition of the solution of residue (5) over a period of 30 minutes. The stirring is then continued at room temperature overnight. Poured into 1000 mL cold water, extracted with 3×150 mL benzene, the continued benzene extracts are washed with 300 mL water, dried over MgSO₄, filtered, and the benzene is stripped at reduced pressure, leaving 44 g of a pale yellow syrup. The product (3) is used in Step 5.

Step 5: Trans-2-[o-fluoroanilino]-5-methylcinnamic acid

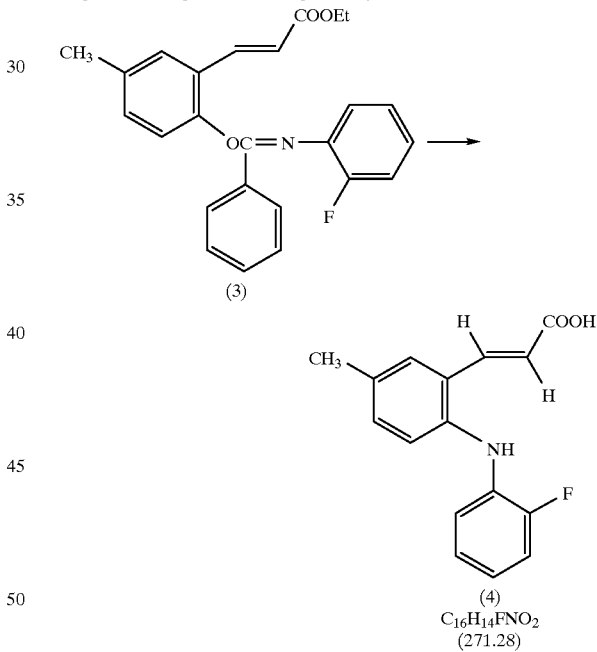

(4)
C₁₆H₁₄FNO₂
(271.28)

Product (3) is heated to 300° C. using a metal bath. The temperature is measured by a thermometer dipping into the reaction mixture. After being allowed to cool to room temperature, the reaction mixture is taken up in 350 mL ethanol, 50 mL 50% NaOH and 50 mL water are added, the solution is refluxed for 5 hours on a steam bath, and allowed to stand overnight at room temperature. The bulk of EtOH is stripped, the residue taken up in 1000 mL hot water, and the product precipitated with 100 mL concentrated HCl in 200 mL water. The oily precipitate is separated, triturated with 100 mL $CCl_4$, whereupon crystallization occurs. The solid is collected (after 3 hours), washed with $CCl_4$. Recrystallized from 100 mL EtOH and 100 mL water (Norite added) and washed with 50% EtOH, and dried in vacuo at 80° C. for 5 hours. Yield: 6.1 g dark yellow solid (4), mp 167–170° C.

Analysis Calculated for: C, 70.85%; H, 5.20%; N, 5.17%. Found: C, 70.82%; H, 5.11%; N, 4.98% (hard to burn).

Any phospholipase $A_2$ inhibitor can be utilized according to this invention to block intestinal absorption of cholesterol and thereby to reduce levels of cholesterol in the blood stream of animals. In addition to the compounds described above, numerous other compounds are known which have been shown to inhibit phospholipase $A_2$. Phospholipase $A_2$ is well-known as a hydrolase enzyme that causes cleavage at the 2-position of glycerophospholipids to produce fatty acids and lysophospholipids. A phospholipase $A_2$ inhibitor is any compound that reduces such hydrolysis. Many different types of organic molecules are known to be inhibitors of phospholipase $A_2$, for example as described by Wilkerson in *Drugs of the Future*, 15, (2):140–147(1990) which is incorporated herein by references for its teaching of such inhibitors. All that is required to effect a reduction in blood cholesterol levels according to this invention is to administer an effective amount of a pancreatic phospholipase $A_2$ inhibitor. Commonly utilized inhibitors will include 4-amino butyrophenones, fluoroketones, aminoamides, benzylamines, benzoxapines, epoxides, arachidonic acid derivatives, alkylamines, retinoids, polyenes, hydroxyketones, 1,4-dihydropyridines, aromatic thioethers, sulfides, heterocyclic amides, quinones, cyclic hydrocarbon amines, aliphatic thioethers, and α-hydroxy thioethers, glycerol derivatives, phospholipids, as well as peptides such as plipastatin and the like. Other phospholipase $A_2$ inhibitors are described by Beaton, et al., *J. Med. Chem*, 37, (5): 557–559 (1994), which also is incorporated herein by reference.

Numerous methods are available for determining whether a particular compound can be classified as a pancreatic phospholipase $A_2$ inhibitor. For example, Reynolds, et al., *Methods In Enzymology*, 197:3–23, describe a variety of assays specifically applicable for phospholipase $A_2$. The assays include physical assays such as titrametric and spectroscopic techniques, as well as biological assays such as those utilizing *E. coli* and coenzyme A—coupled assays. Any of the art recognized assays can be employed to determine if a particular compound will be effective as an inhibitor of the pancreatic phospholipase $A_2$ enzyme. Any compound that can be shown to be an inhibitor of pancreatic phospholipase $A_2$ can be utilized in this invention to reduce blood levels of cholesterol by inhibiting intestinal absorption of cholesterol.

The present invention in a further embodiment includes a pharmaceutical composition for the treatment of hypercholesterolemia and/or coronary artery disease which comprises administering an effective amount of a pancreatic phospholipase $A_2$ inhibitor compound described above or a pharmaceutically acceptable salt thereof, together with a pharmaceutically acceptable carrier for the treatment of the condition. The term "condition" is meant to include atherosclerosis, coronary artery disease, etc.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups, or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide pharmaceutically elegant and palatable preparations. Tablets contain the active ingredient in admixture with non-toxic pharmaceutically acceptable excipients which are suitable for the manufacture of tables. These excipients may be, for example inert diluents, such as calcium carbonate, sodium carbonate, lactose, calcium phosphate, or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glycerol monostearate, or glycerol distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexethal such as polyoxyethylene sorbitol monooleate, or condensation products of ethylene oxide with partial esters derived from fatty acids and hexethal anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid. Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be vegetable oil, for example, olive oil or arachis oil, or a mineral oil, for example, liquid paraffin or mixtures of these. Suitable emulsifying agents may be naturally-occurring gums, for example, gum acacia or gum tragacanth, naturally-occurring phosphatides, for example, sorbitan monooleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol, or sucrose. Such formulations may also contain a demulcent, a preservative, and flavoring, and coloring agents. The pharmaceutical compositions may be in the form of a sterile injectable aqueous or oleaginous suspension. This suspension may be formulated according to the known art using those suitable dispersing or wetting agents and suspending agents which have been mentioned above.

Dosage levels of the pancreatic phospholipase $A_2$ inhibitor on the order of from about 0.01 mg to about 150 mg per kilogram of body weight per day are useful in the treatment of the above-indicated diseases (about 0.5 mg to about 7.5 g per patient per day). For example, hypercholesterolemia may be effectively treated by the administration of from about 0.2 to 50 mg of the pancreatic phospholipase $A_2$ inhibitor compound per kilogram of body weight per day (about 20 mg to about 3.5 g per patient per day). Preferably a dosage of from about 1 mg to about 20 mg per kilogram of body weight per day may produce good results (about 25 mg to about 1 g per patient per day).

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of a carrier material which may vary from about 5 to about 95 percent of the total composition. Dosage forms will generally contain between from about 1 mg to about 500 mg of an active ingredient.

For use in treatment of hypercholesterolemia or coronary artery disease, the pancreatic phospholipase $A_2$ inhibitor can be administered orally when it is appropriate. The dose administered can be from as little as 0.1 to 25 mg or more per day, singly, or preferably on a 2 to 4 dose per day regimen although a single dose per day is satisfactory. In oral administration, the drug can be employed in any of the usual dosage forms such as tablets or capsules, either in a contemporaneous delivery or sustained release form. Any number of the usual excipients or tableting aids can likewise be included.

Thus, in a solution, insert, suspension, or a tablet, the active medicament or an equivalent amount of a salt thereof is employed, the remainder being carrier, excipient, preservatives and the like as are customarily used in such compositions.

As with all medications, dosage requirements are variable and must be individualized on the basis of the disease and the response of the patient.

The present invention in a still further embodiment includes a method for treatment of the condition as noted above in mammals, including humans, suffering therefrom by administering a pancreatic phospholipase $A_2$ inhibitor, including a compound of the following Formulas I–VI:

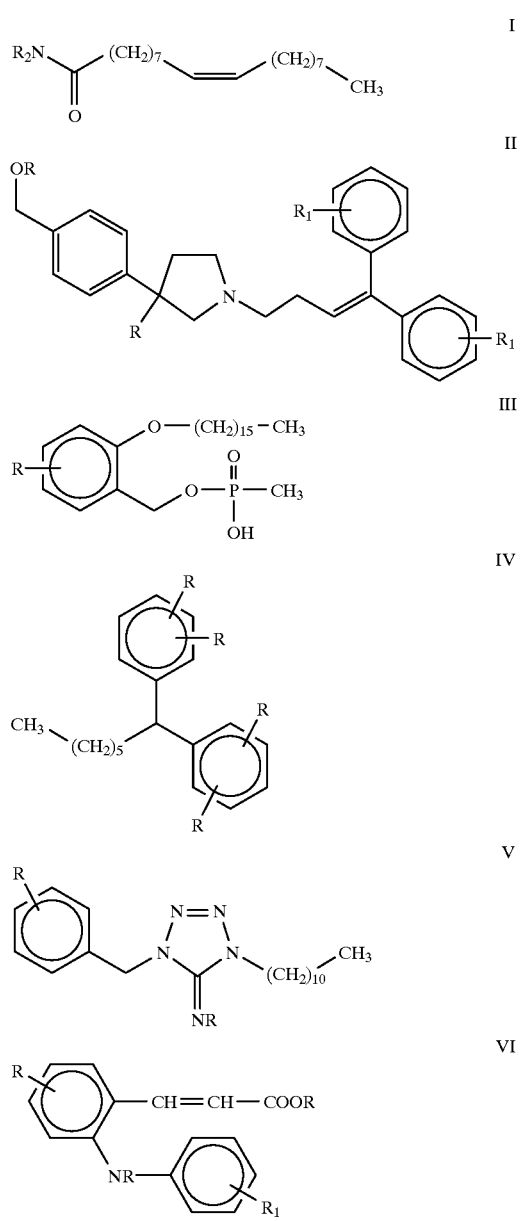

or a pharmaceutically acceptable salt thereof in unit dosage form. The method of treatment described above using the pharmaceutical compositions or the compounds or salts of Formulas I–VI is meant to include prophylactic treatment of the foregoing condition.

Preferred compounds of Formulas I–VI employed as an active agent in a pharmaceutical composition in the method of treatment are selected from the group consisting of:

4,4'-heptylidenebis-2-methyl-phenol;

1,4-dihydro-1-(phenylmethyl)-4-undecyl-5H-tetrazol-5-imine;

1-[4,4-bis(4-fluorophenyl)butyl]-3-(3-methoxyphenyl)-3-methylpyrrolidine;

methyl-[2-(hexadecyloxy) phenylemethyl]ester phosphonic acid;

9-octadecenamide, particularly the (Z) form;

2-(m-chloroanilino)-5-methyl-cinnamic acid, particularly the transform; and 2-(o-fluoroanilino)-5-methyl-cinnamic acid, particularly the transform.

Data Supporting Conclusion that Hydrolysis of PC by Phospolipase $A_2$ is a Step in the Initiation of Intestinal Lipid Absorption The conclusion that the hydrolysis of PC by pancreatic phospholipase $A_2$ (hereinafter "$PLA_2$") is the critical step in the initiation of intestinal lipid absorption is supported below by experiments exploring the effects of micellar PC on lipid absorption by cultured enterocytes (Caco-2) and the effect of $PLA_2$ inhibitors on lipid absorption in lymph-fistula rats and cholesterol-fed rats.

BRIEF DESCRIPTION OF THE DRAWINGS

FIG. 3 shows that phospholipids have little effect on cellular absorption and metabolism of fatty acids.

FIG. 6 shows that cellular absorption and metabolism of retinol is not affected by the presence of phospholipids or pancreatic phospholipase $A_2$.

I. CACO-2 CELL STUDIES

Caco-2 cells were used as a tissue culture model of the human intestinal epithelium to compare the effects of phosphatidylcholine and lysophosphatidylcholine on lipid absorption and the subsequent re-esterification and secretion of micelle-derived lipids. Caco-2 cells are derived from a human colon adenocarcinoma and spontaneously form polarized cell monolayers in culture which exhibit many of the morphological and functional characteristics of normal enterocytes including the production and polarized secretion of lipoproteins synthesized from absorbed lipids (Traber M. G, Kayden H. J., and Rindler M. J., Polarized secretion of newly synthesized lipoproteins by the Caco-2 human intestinal cell line, *J. Lipid Res.*, 28:1350–1363 (1987); Field F. J., Albright E., and Mathur S. N., Regulation of triglyceride-rich lipoprotein secretion by fatty acids in Caco-2 cells, *J. Lipid Res.*, 29:1427–1437 (1988)).

Lipid Absorption Versus Micellar Phospholipid Composition

Caco-2 cell monolayers, grown on micropore membranes separating apical and basolateral culture solutions, were incubated with taurocholate, mixed-lipid micelles composed of 5 mM taurocholic acid, 300 μM monooleoylglycerol, 500 μM [$^3$H]oleic acid, 100 μM [$^{14}$C]cholesterol, and 200 μM phospholipid consisting of various proportions of 1-palmitoyl-2-oleoyl phosphatidylcholine and 1-palmitoyl lysophosphatidylcholine. The micelles were added to the apical side of the cell monolayers. Phospholipid-free micelles were also tested for comparison. At the end of 6 hours of incubation, the radiolabeled lipid content of the cells and in the basolateral media were determined. Phospholipid content strongly influenced the absorption and metabolism of cholesterol (FIGS. 1, 2) but had only minimal effects on fatty acid uptake and metabolism (FIG. 3). Caco-2 monolayers incubated with micelles containing only phosphatidylcholine as the phospholipid absorbed 65% less [$^{14}$C]cholesterol than cell monolayers incubated with phospholipid-free micelles. Substitution of lysophosphatidylcholine for phosphatidylcholine reversed this effect, but only when the mole fraction of micellar lysophosphatidylcholine was greater than 50%.

Figure 1C:
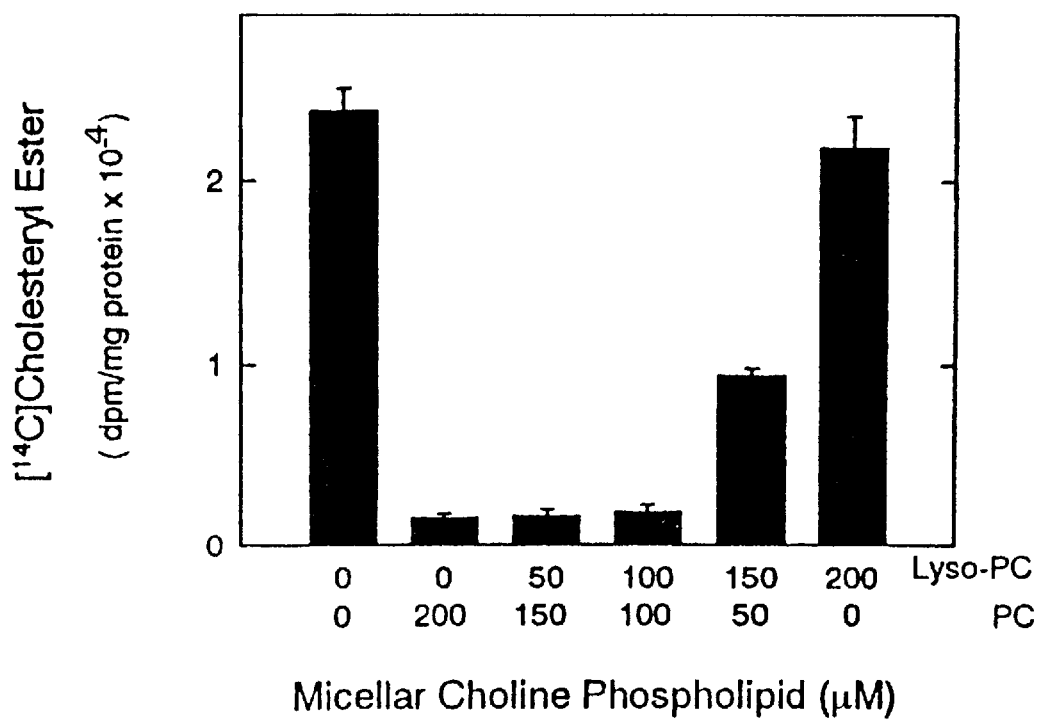
FIGS. 1 and 2 show the suppression of absorption and metabolism of cholesterol in cells caused by the presence of a phospholipid.
Figure 2C:
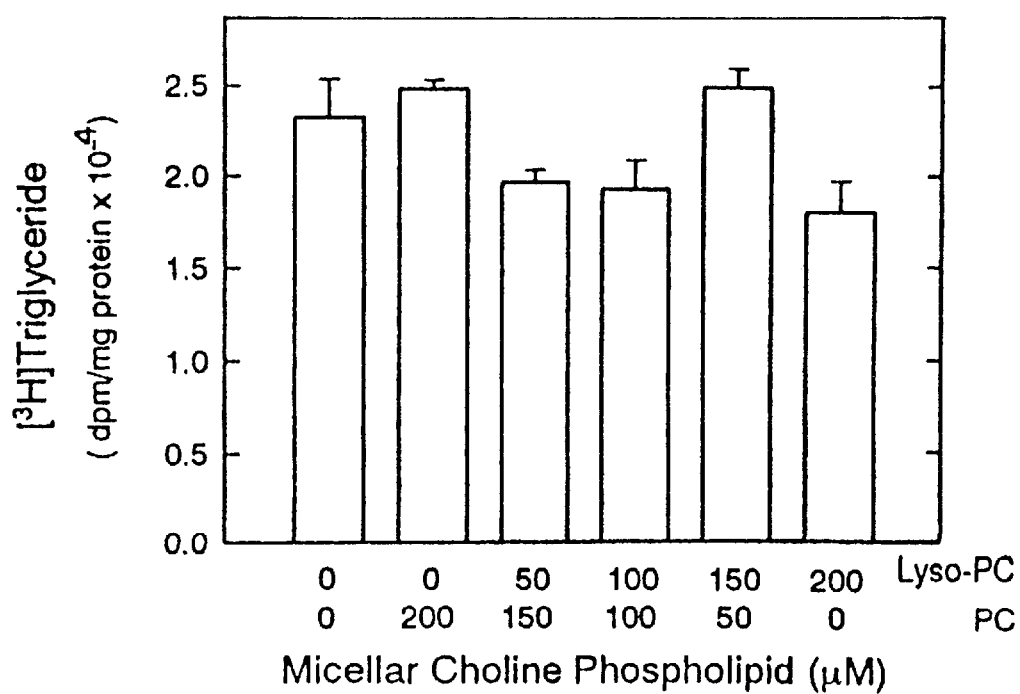

In contrast to the results for cholesterol uptake, micellar phospholipid composition had no significant effect on the uptake of micellar [$^3$H]oleic acid. Greater than 95% of the [$^3$H]oleic acid transferred to the cells was incorporated into the cellular acylated lipids, of which greater than 92% comprised [$^3$H]-labeled TG and PC. As FIG. 3 shows, [$^3$H]oleic acid incorporation into TG and PC was essentially unaffected by micellar phospholipid composition. Acyl-CoA:cholesterol acyl transferase (ACAT) activity was diminished in cells incubated with PC-containing micelles (FIGS. 1B, 1C), even though the results for TG and PC synthesis suggest the cellular supply of [$^3$H]oleoyl-CoA available to acyl transferases was not modified by micellar phospholinid composition. The reduction in ACAT activity, as measured by [$^3$H]oleic acid incorporation, was directly correlated to the supply of micellar cholesterol entering the cells (FIGS. 1A, 1B). Compared to the incubations with phospholipid-free micelles, incubations with micelles containing 50% or more of choline lipid in the form of PC resulted in 65% less cholesteryl [$^3$H]oleate synthesis. Esterification of micellar [$^{14}$C]cholesterol was reduced to an even greater extent (FIG. 1C).

Lipid secretion was directly dependent on cellular lipid synthesis. As the data plotted in FIG. 2 indicate, the cellular secretion of radiolabeled lipid metabolites into the media on the basolateral side of the Caco-2 cell monolayer correlated directly with the variations in cellular lipid synthesis that resulted from modification of micellar phospholipid composition (FIG. 1).

Phospholipase $A_2$—Dependent Cholesterol Absorption

Figure 4C:
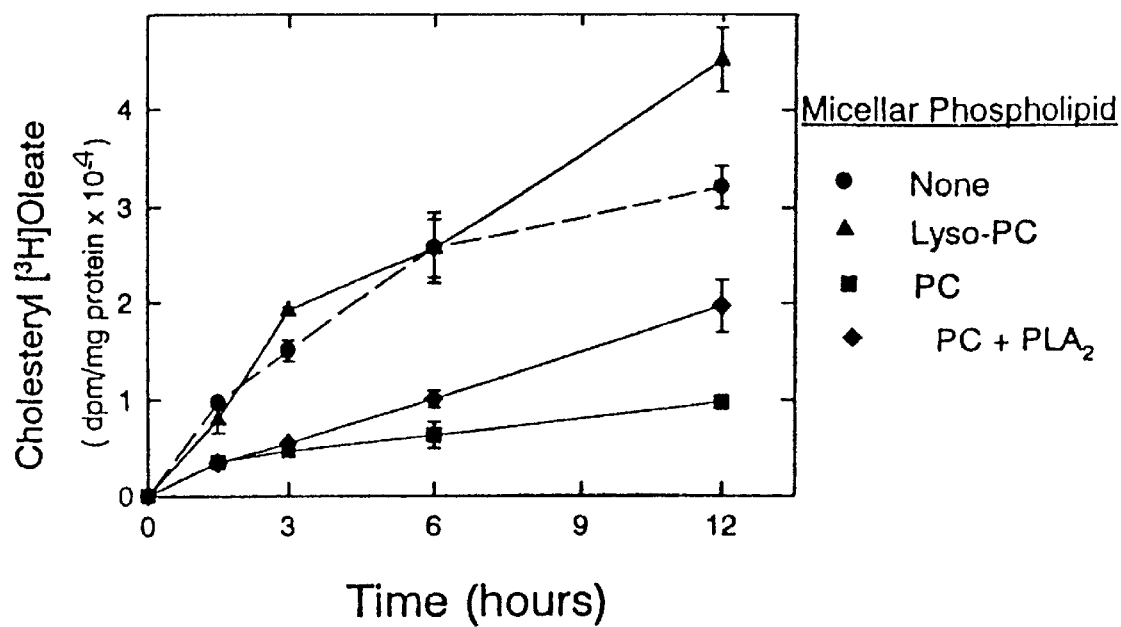
FIG. 4 shows that addition of pancreatic phospholipase $A_2$ reverses the suppression of cholesterol absorption and metabolism caused by phospholipids.

The addition of porcine pancreatic phospholipase $A_2$ to incubations of Caco-2 monolayers with PC-containing micelles reversed the suppression of cholesterol absorption. This is shown in FIG. 4, where the time-course of micellar [$^{14}$C]cholesterol absorption and esterification is compared for Caco-2 monolayers incubated with micelles containing no phospholipid, lyso-PC, PC or PC in the presence of $PLA_2$. In all cases. the major portion (approximately 90%) of micellar [$^{14}$C]cholesterol taken up by the cells remained unesterified throughout the 12-hour incubation period. In the case of monolayers incubated with phospholipid-free or lyso-PC-containing micelles, cellular free [$^{14}$C]cholesterol was at steady-state levels after 3 hours of incubation. In contrast, at most 45% of that level of cell-associated [$^{14}$C] cholesterol was obtained after 12 hours of incubation for cells given PC-containing micelles. This was increased to 76% of the level obtained in the absence of PC by the addition of PLA$_2$ to the incubations with PC-containing micelles. Cellular [$^{14}$C]cholesterol esterification was even more severely affected by micellar phospholipid composition. By 12 hours, cell levels of [$^{14}$C]cholesteryl ester, relative to incubations without micellar phospholipid, were 152%, 7%, and 60% for incubations with micelles containing lyso-PC, PC or PC in the presence of PLA$_2$, respectively. Thus, PLA$_2$ partially reversed the inhibitory effects of micellar PC.

Figure 5A:
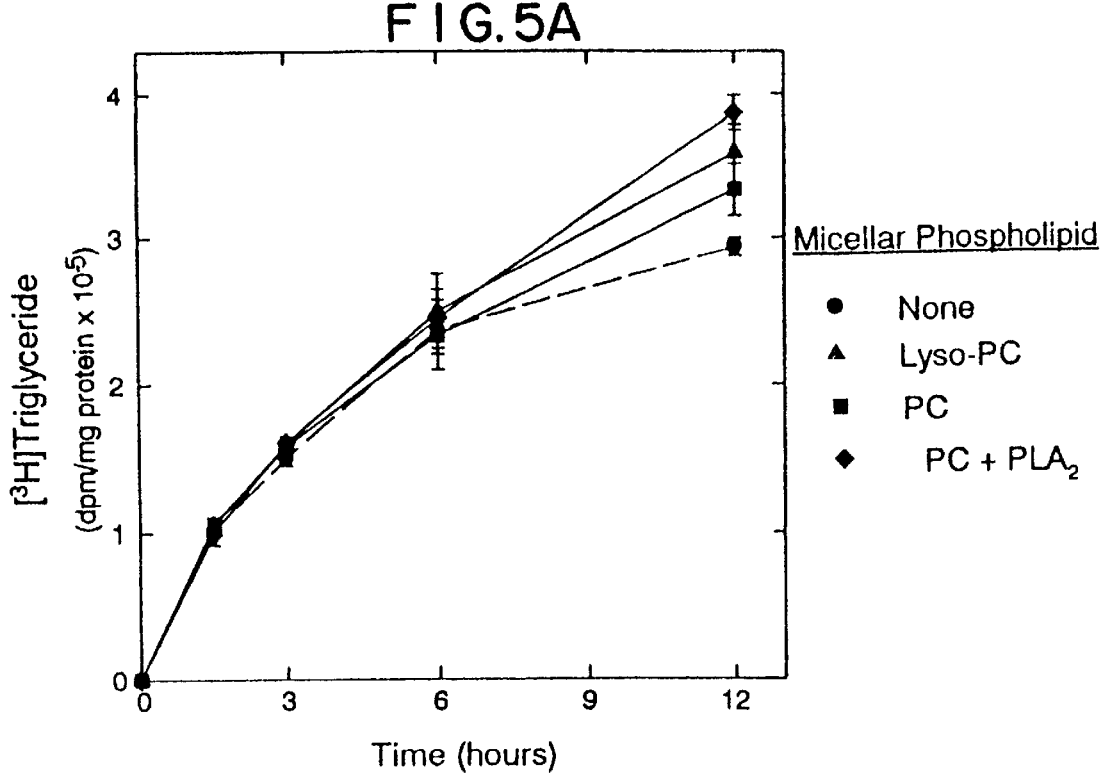
FIG. 5 shows the lack of effect on fatty acid absorption caused by phospholipids alone or together with a pancreatic phospholipase $A_2$.
Figure 5B:
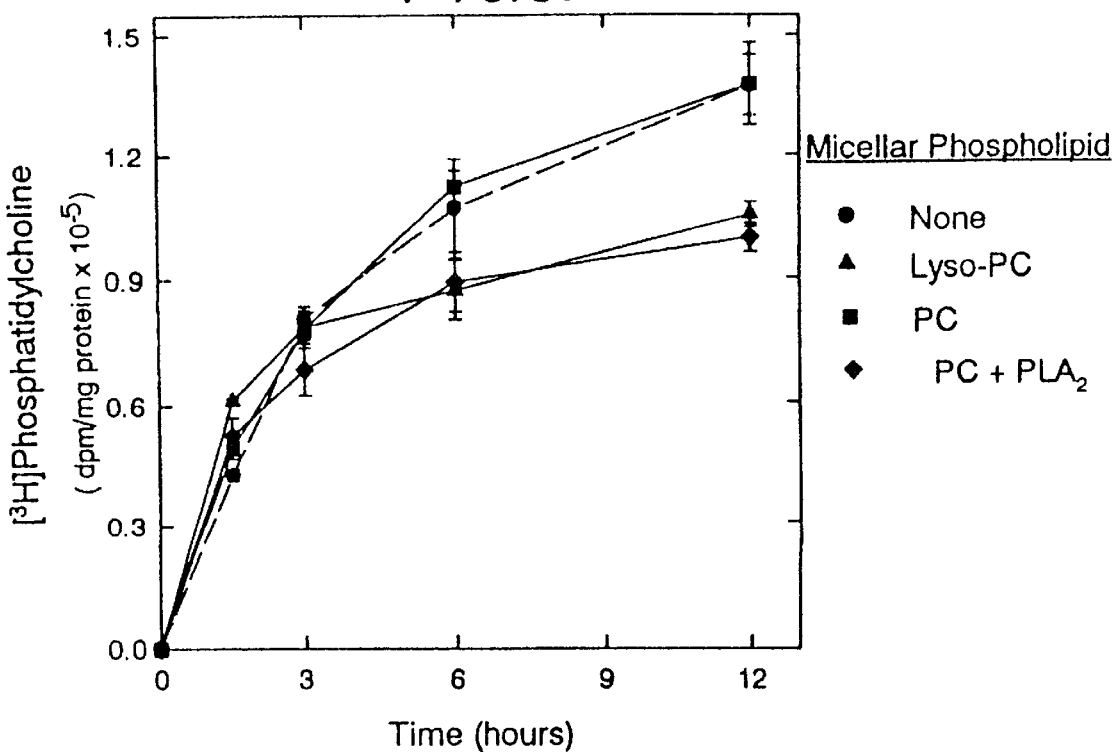

In contrast to the results for micellar [$^{14}$C]cholesterol absorption, micellar [$^3$H]oleic acid uptake and metabolism were only slightly affected by micellar phospholipid composition (FIG. 5). Cellular accumulation of [$^3$H]oleate-labeled triglyceride, which was the major cellular product formed from absorbed [$^3$H]oleic acid, was not significantly affected by micellar phospholipid composition (FIG. 5A). Relative to phospholipid-free micelle incubations, a slight decrease in [$^3$H]oleate-labeled PC synthesis was detected after 6 hours of incubation with micelles containing lyso-PC or PC with PLA$_2$ (FIG. 5B). Possibly, cellular PC acylation is reduced by the increased supply of micelle-derived lysoPC that can be utilized as an acylated precursor for PC synthesis.

Retinol Absorption

The micelle preparations used in the experiments described for FIG. 4 also contained 10 μM retinol. Retinol was included to determine whether the influence of micellar phospholipid composition on cholesterol absorption extended to other fatty alcohols. Like cholesterol, retinol is a fatty alcohol that is absorbed from the diet by the intestinal epithelium and passed into the circulation by an analogous transport process involving fatty acylation and assembly of the resultant retinyl esters into chylomicrons (Blomhoff R., Green M. H., Berg T., Norum K. R., "Transport and storage of vitamin A." *Science*, 250:399–404 (1990)). Surprisingly, in the same experiments, where [$^{14}$C]cholesterol absorption was blocked by micellar PC (FIG. 4), retinol uptake and esterification were unmodified by changes in micellar phospholipid composition (FIG. 6).

Lipase Studies

Figure 7A:
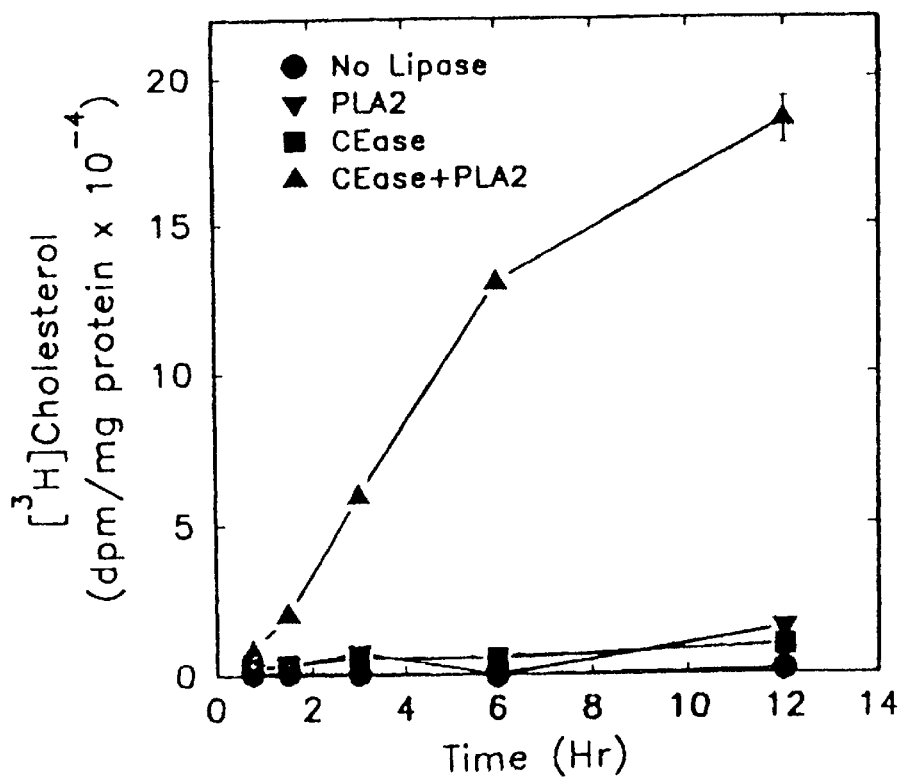
FIGS. 7 and 8 show that the presence of pancreatic phospholipase $A_2$ causes a dramatic increase in cellular absorption of fatty acids.
Figure 7B:
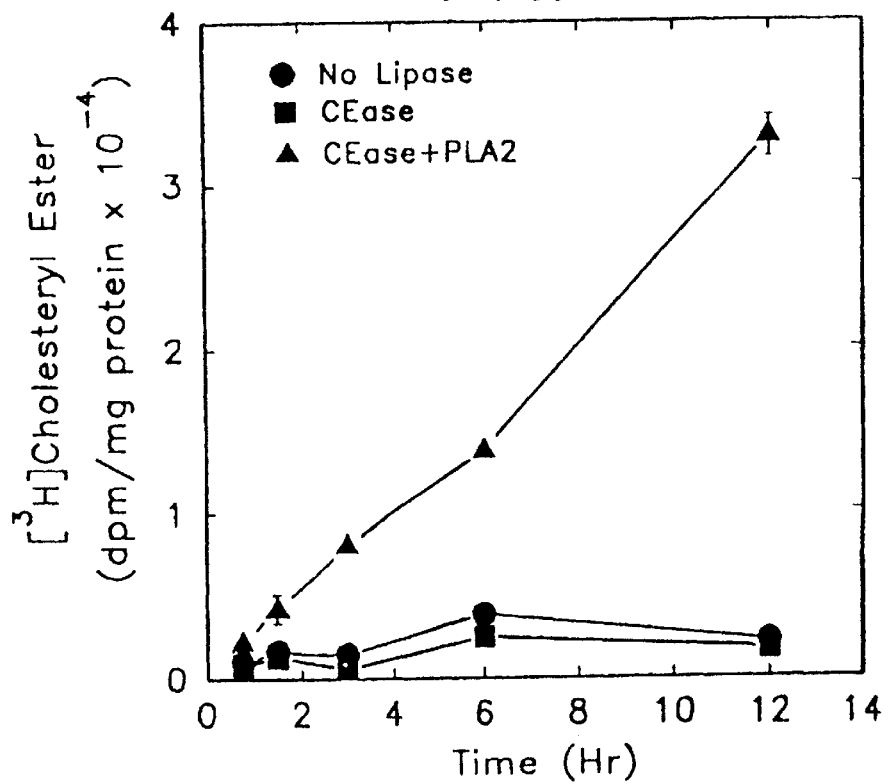
Figure 8A:
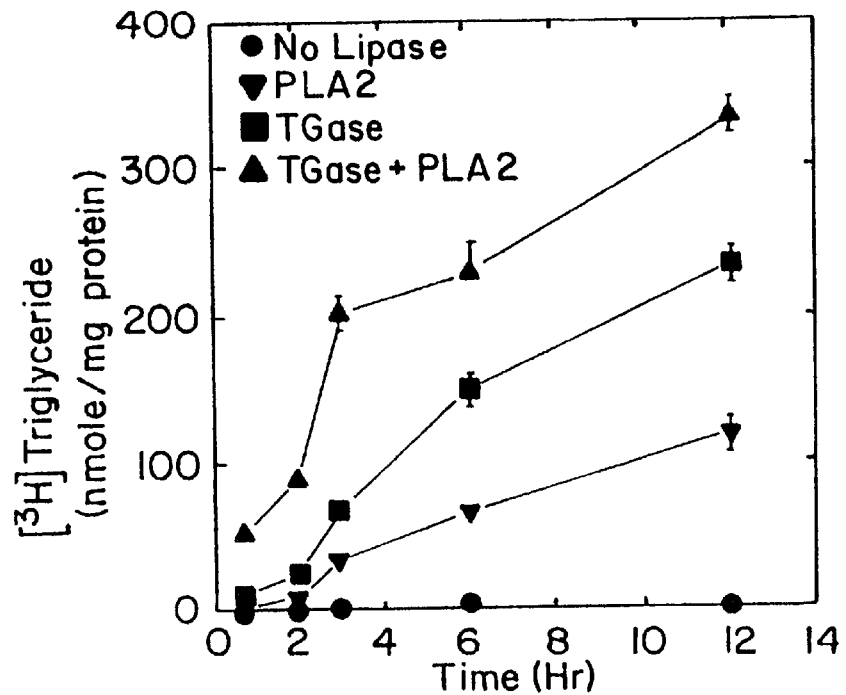
Figure 8B:
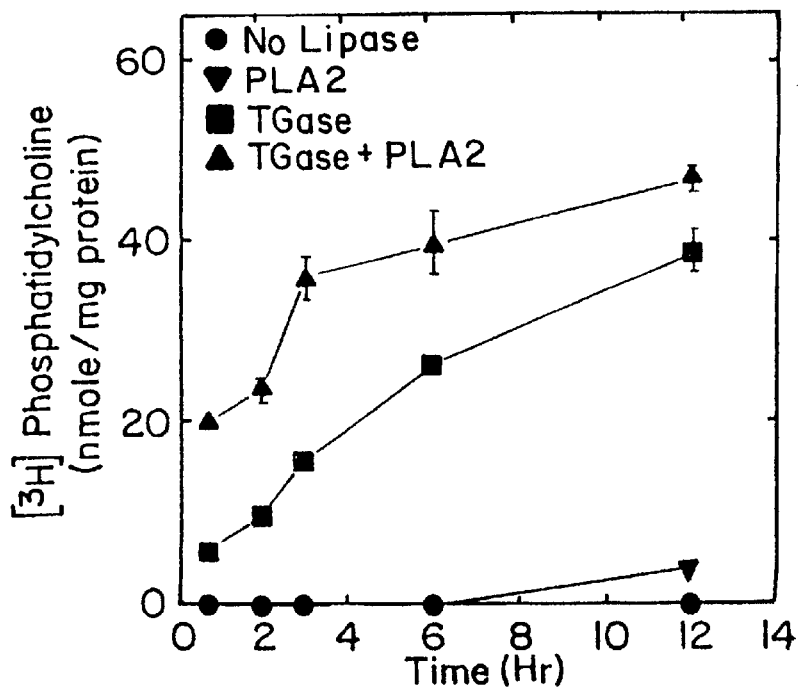

The work by Borgstrom and coworkers suggests that the activities of triglyceride lipase and carboxyl ester lipase towards the corresponding micellized substrates are also dependent on PC degradation by PLA$_2$ (Borgstrom B., "Importance of phospholipids, pancreatic phospholipase A$_2$ and fatty acid for the digestion of dietary fat." *Gastroenterology*, 78:954–962 (1980)). This was tested with the Caco-2 cells. Taurocholic acid micelles containing phosphatidylcholine, triolein, cholesteryl oleate and cholesterol were placed in the medium covering the apical surface of Caco-2 cell monolayers. Depending on the neutral lipid lipase being studied, either the triolein or cholesteryl oleate was tritium-labeled. The time course of radiolabeled lipid uptake and metabolism was studied in the absence or presence of the neutral lipid lipases, with or without PLA$_2$. The results for carboxyl ester lipase and triglyceride lipase are presented in FIGS. 7 and 8, respectively. The results are in agreement with those presented by Borgstrom and coworkers. The micellar [$^3$H]cholesteryl oleate label did not enter the cells unless both carboxyl ester lipase and PLA$_2$ were included in the incubation. The results for micellar tri[$^3$H]olein uptake indicated a similar but less severe dependence of triglyceride lipase activity on PLA$_2$. Tritium label did enter the cells in incubations performed with either lipase alone, but the greatest cellular accumulation of tritiated lipid occurred in the incubation containing both lipases together.

II. Lymph-Fistula Rat Studies

The intestinal lipid absorption pathway was isolated in the rat by inserting an infusion cannula in the proximal duodenum and implanting a second cannula in the mesenteric lymph vessel to intercept the lipoprotein output from the intestine. This lymph-fistula rat model was used to investigate the effect of pancreatic PLA$_2$ inhibition, in situ, on intestinal absorption of infused lipid emulsions. In a typical experiment, cannulae were implanted the day before the experimental infusion. Following surgery, the animals were infused (2.5 mL/hr) with isotonic saline containing dextrose to flush the GI tract and obtain basal levels of lymphatic lipid output. On the day of the experiment, infusion of the dextrose recovery solution was continued for 1 hour to collect a basal lymph fraction. At the start of the next hour, the intake of the duodenal infusion cannula was switched to a lipid emulsion of isotonic saline containing safflower oil (59 mM), cholesterol (5.2 mM), PC (3.3 mM) and taurocholic acid (1.9 mM). One hour lymph fractions were collected until the end of the experiment. The lipid content (mass) of lymph fractions was determined by HPLC with a mass-sensitive, evaporative light-scattering detector.

Effect of Micellar Diester and Diether PC Analogs on Lipid Absorption

Figure 9A:
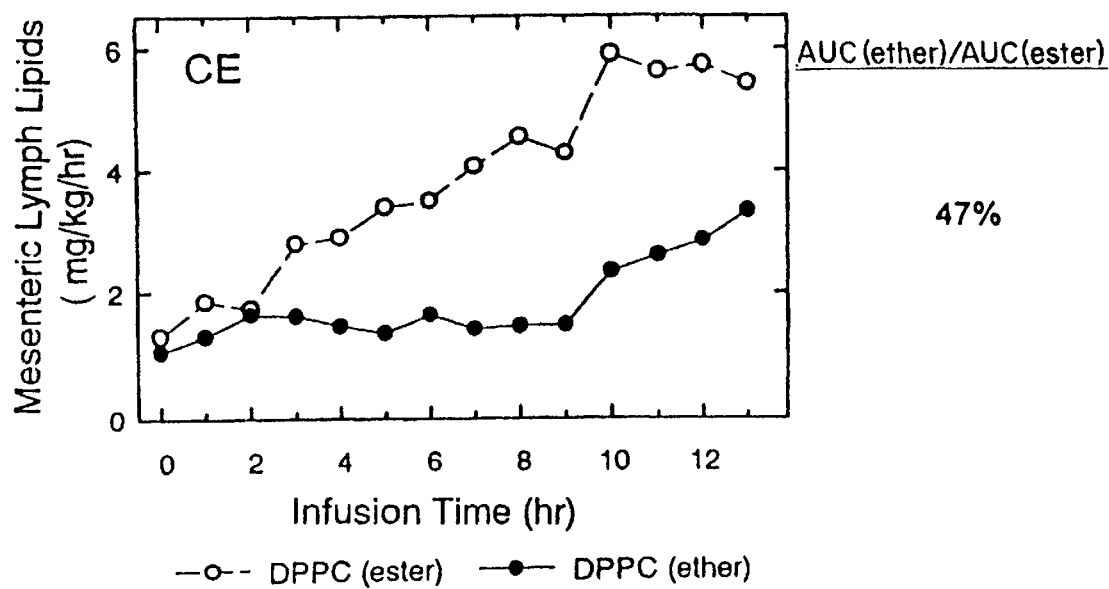
FIG. 9 shows that the presence of nonhydrolyzable phospatidylcholine prevents absorption of lipids into cells.
Figure 9B:
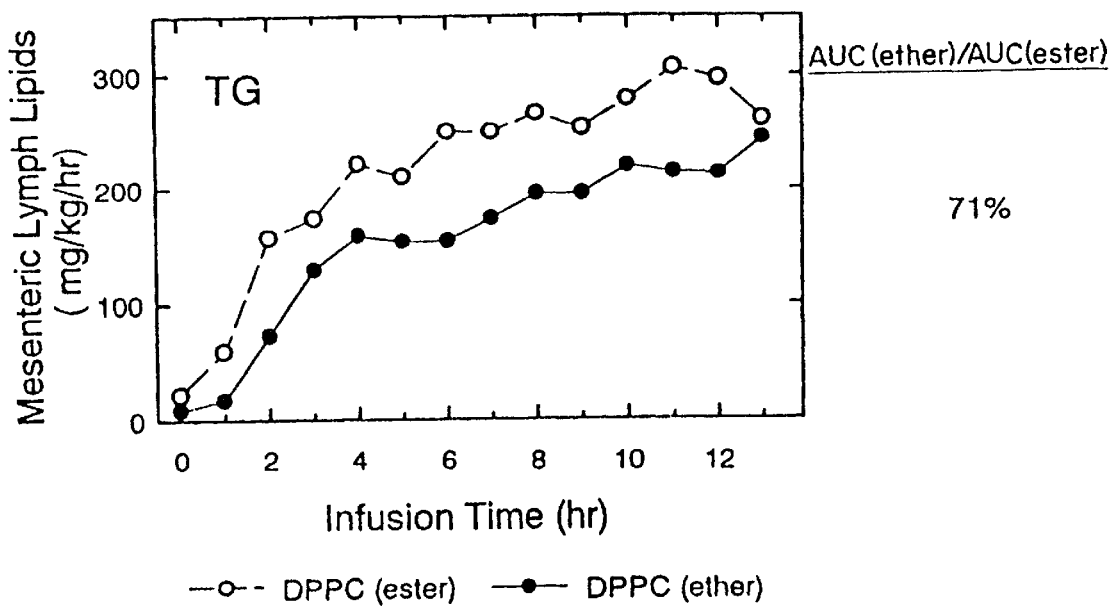
Figure 9C:
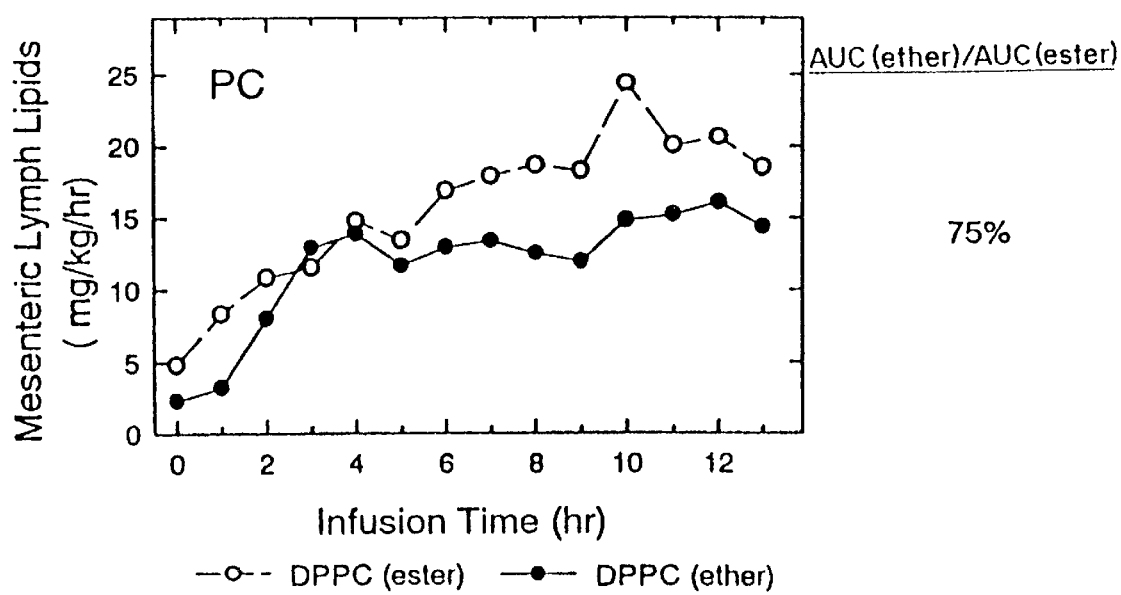

PC analogs in which the normal acyl chains are replaced by alkyl carbon chains linked to the glycerol backbone by ether bonds have physical-chemical properties similar to conventional diester PC molecules but are not hydrolyzable by PLA$_2$. To determine the significance of micellar PC hydrolysis in intestinal lipid absorption, a comparison was made of the mesenteric lymph lipid output from rats infused with lipid microemulsions prepared with 1,2-dipalmitoyl PC (DPPC(ester)) or 1,2-dipalmityl PC (DPPC(ether)) as the PC constituent. The results are plotted in FIG. 9 and show that lymphatic cholesteryl ester (CE) output was greatly reduced with infusions of DPPC(ether) compared to infusions with DPPC(ester). In fact, unlike the DPPC(ester) infusions, lymphatic cholesteryl ester output with DPPC(ether) infusion did not rise above basal output levels until 8 hours after the initiation of lipid emulsion infusion. The total lymphatic CE output over the 12-hour period of DPPC(ether) infusion was only 47% of total CE output obtained with the DPPC (ester) emulsion.

Intestinal output of TG and PC into the mesenteric lymph were also reduced by the diether PC analog. The total outputs of TG and PC for DPPC(ether) infusion were 71% and 75%, respectively, relative to DPPC(ester) infusions. Unlike the result for CE secretion, the onset of the rise in lymphatic TG and PC output following initiation of lipid infusion was not delayed by DPPC(ether). These results support the hypothesis that intestinal lipid absorption is dependent on degradation of lumenal PC.

Effect of PLA$_2$ Inhibitors on Lipid Absorption

An alternate method to preserve PC in the intestinal contents so that the effects of intact PC on lipid absorption can be evaluated is to render pancreatic PLA$_2$ inactive with specific inhibitors. The effects of two PLA$_2$ inhibitors [1,4-dihydro-1-(phenylmethyl)-4-undecyl-5H-tetrazol-5-imine (Compound B) and methyl-1-[2-(hexadecloxy)phenyl] methyl ester phosphonic acid (Compound D) were tested on lipid absorption in lymph-fistula rats. The collection of basal lymph samples and infusion of lipid emulsion was essentially as that described above except that egg PC was used as the PC component of the emulsion. The inhibitors were introduced to the intestinal tract of test animals as part of the lipid emulsion infusate. After 1 hour of infusion with dextrose/saline for collection of basal lymph, the duodenal cannulae intakes were transferred to lipid emulsions containing the inhibitor (test rats) or lipid emulsions containing the vehicle used to solubilize the inhibitor (control rats). The total amount of inhibitor infused was 30 mg/kg. It was included in 7.5 mL of emulsion and infused over the course of 3 hours. When infusion of inhibitor/emulsion or vehicle/emulsion mixtures was complete, the duodenal cannulae intakes were transferred to plain lipid emulsion for the remainder of the experiment.

Figure 10A:
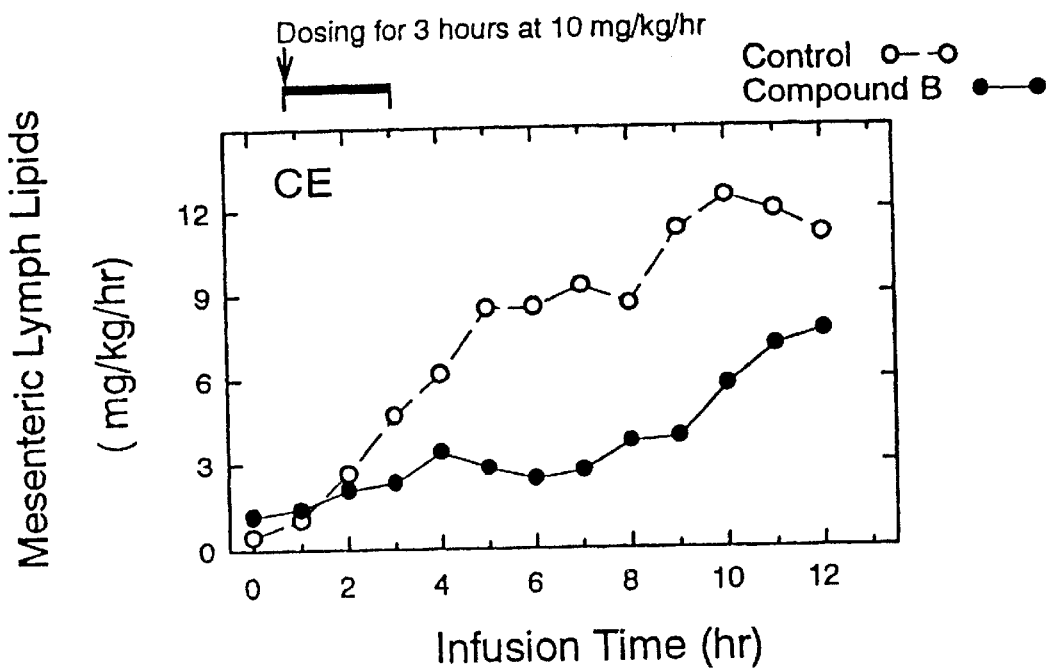
FIG. 10 shows that lipid absorption in rats is reduced in the presence of $PLA_2$ inhibitor 1,4-dihydro-1-(phenylmethyl)-4-undecyl-5H-tetrazol-5-imine, Compound B.
Figure 10B:
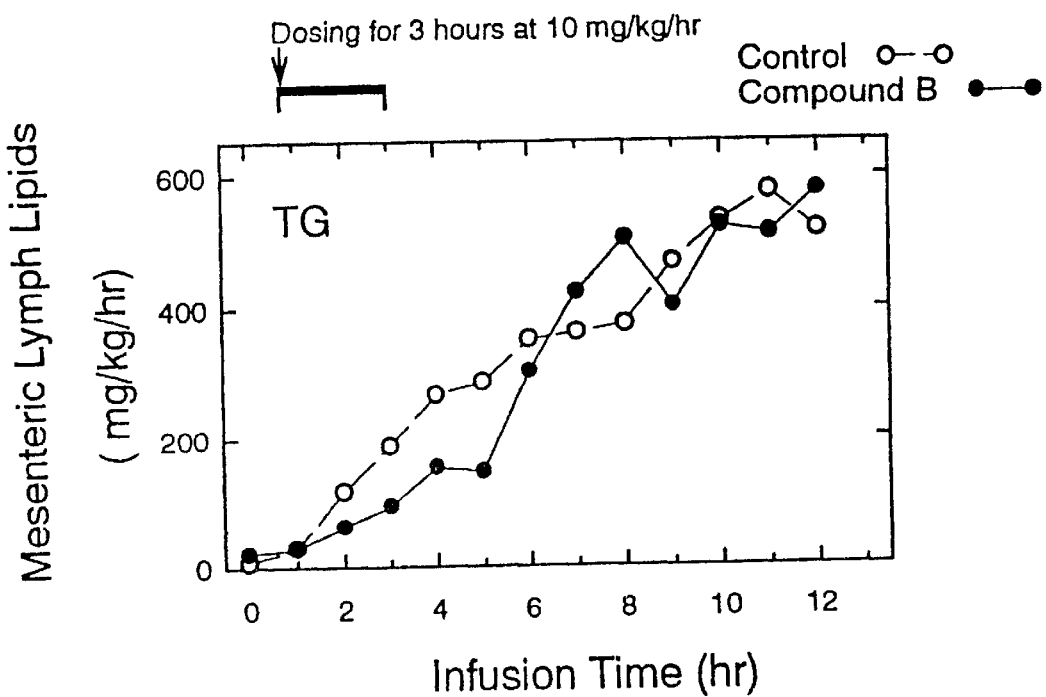
Figure 10C:
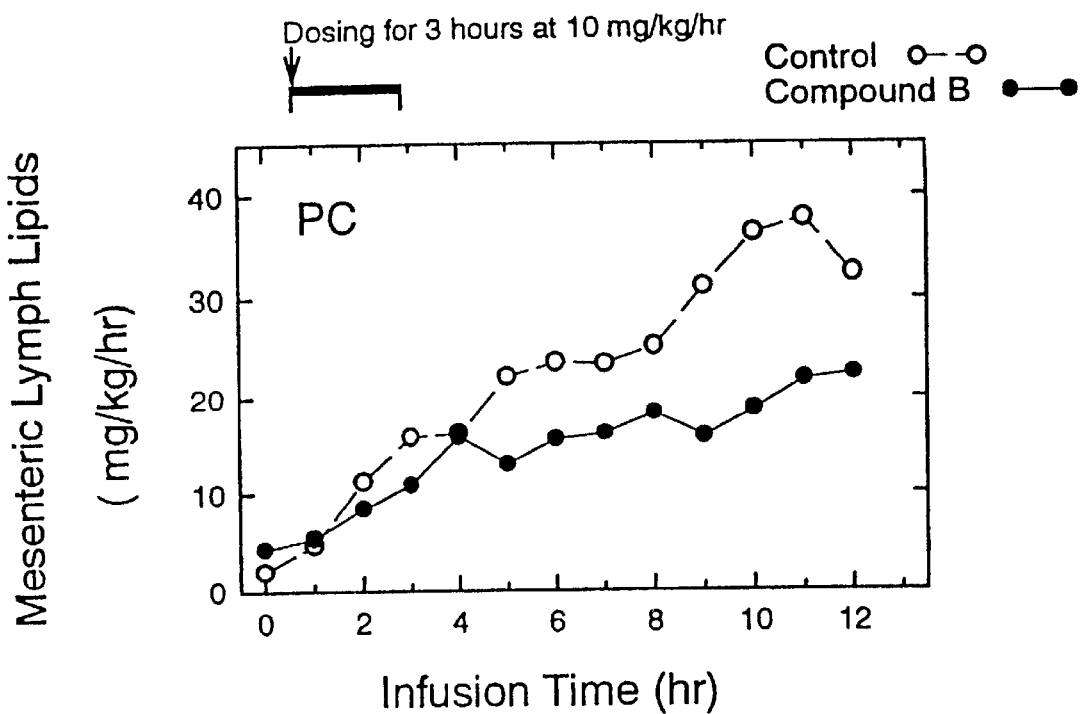
Figure 11A:
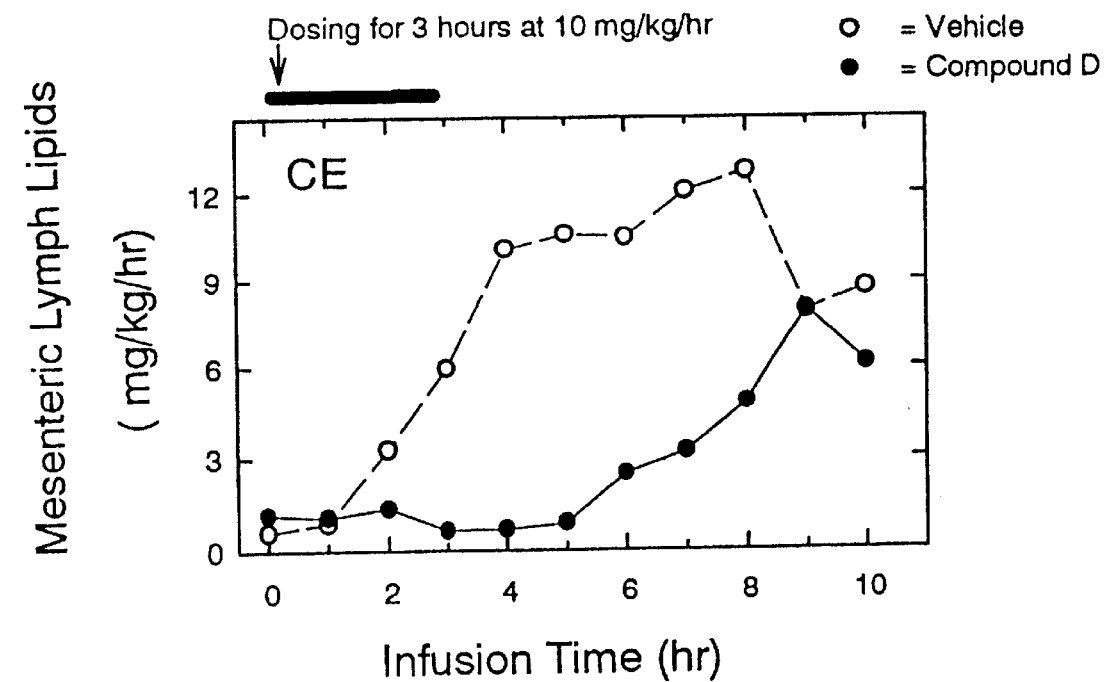
FIG. 11 shows that lipid absorption is reduced in rats in the presence of $PLA_2$ inhibitor methyl [2-(hexadecyloxy)phenyl]methyl phosphonate, Compound D.
Figure 11B:
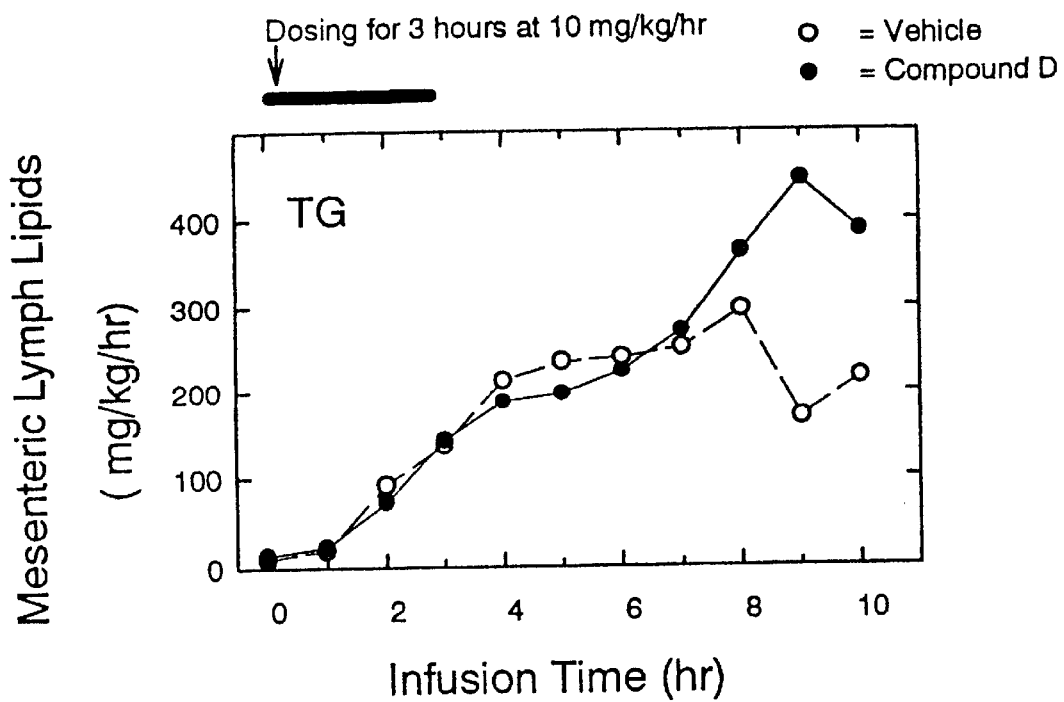
Figure 11C:
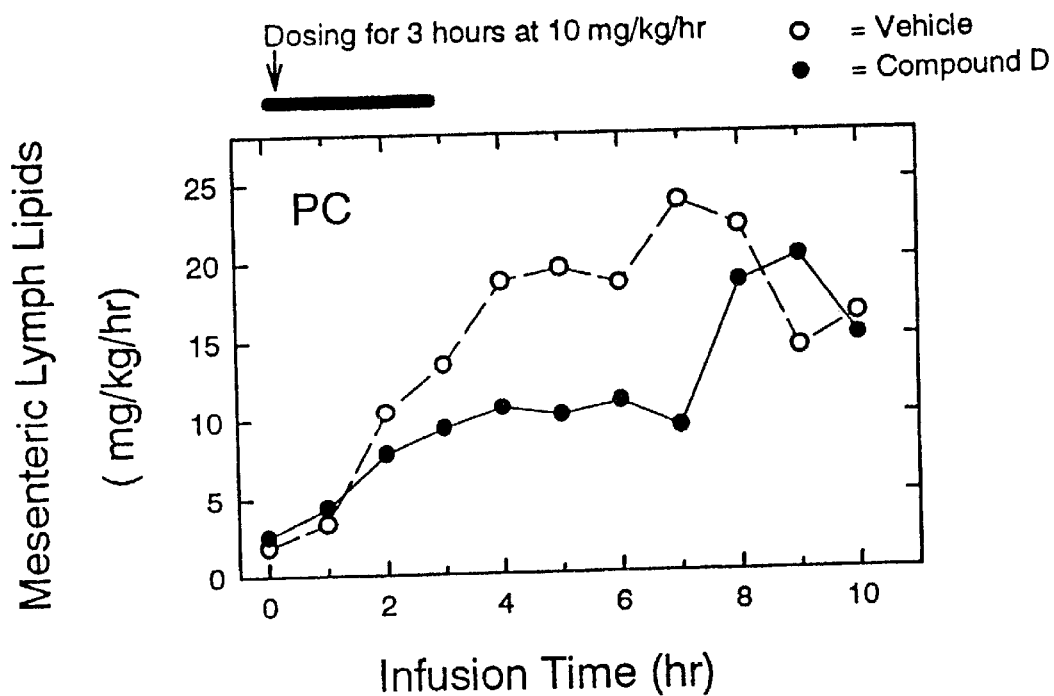

The lipid emulsion-dependent rise in lymphatic CE output obtained with control infusions was greatly blunted by both inhibitors (FIGS. 10, 11). In contrast, there were no significant reductions in lymphatic TG output with inhibitor treatment. Both inhibitors did cause a significant reduction in the rates of lymphatic PC output, but to a lesser extent than that detected for CE. Both compounds were also tested in an in vitro assay for acyl-CoA:cholesterol acyltransferase (ACAT) to exclude the possibility that the reductions in lymphatic CE output were due to ACAT inhibition, which could also account for the results. Neither compound inhibited the rat liver ACAT used in the in vitro assay.

III. Effect of PLA$_2$ Inhibitors on Plasma Lipids in Cholesterol-fed Rats

Ultimately, agents that inhibit the absorption of dietary cholesterol should suppress postprandial increases in plasma cholesterol. This was tested with several PLA$_2$ inhibitors in cholesterol-fed rats. The general protocol consisted of preparing a carboxymethyl cellulose/Tween 20 dispersion of the compound of interest and administering it at a dose of 100 mg/kg by oral gavage to rats previously trained to meal-feed. Immediately following administration of the inhibitor, the rats were fed a lipid-rich meal of chow supplemented with cholesterol, peanut oil, and cholic acid. Because plasma cholesterol levels typically peak in control animals about 8 hours after the start of feeding, all rats were sacrificed at this time for determination of plasma lipid levels.

The results are presented below in Table 1 and show that orally administered PLA$_2$ inhibitors (Compounds A through G in the table) significantly inhibit diet-induced increases in plasma cholesterol. The IC$_{50}$ values for inhibition of porcine pancreatic PLA$_2$, in vitro, are included for comparison with the in vivo activities.

TABLE 1

| | In Vivo Activity of PLA$_2$ Inhibitors in Cholesterol-fed Rats (% Change in plasma lipids at 100 mg/kg dose vs. Control) | | | | In Vitro IC$_{50}$ (porc. panc. PLA$_2$) |
|---|---|---|---|---|---|
| | Total Chol. | non-HDL Chol. | HDL Chol. | TG | μM |
| Compound A | −24 | −32 | 1 | −11 | 2.2 |
| Compound B | −32 | −44 | 9 | ND | 4 |
| Compound C | −30 | −49 | 38 | ND | 5.7 |
| Compound D | −12 | −17 | 3 | −17 | 3 |
| Compound E | −42 | −56 | 2 | −35 | 2.4 |
| Compound F | −15 | −20 | 2 | −5 | 8.6 |
| Compound G | −12 | −21 | 15 | −24 | 4.6 |

A - 4,4'-heptylidenebis-2-methyl-phenol
B - 1,4-dihydro-1-(phenylmethyl)-4-undecyl-5H-tetrazol-5-imine
C - 1-[4,4-bis(4-fluorophenyl)butyl]-3-(3-methoxyphenyl)-3-methylpyrrolidine
D - methyl-[2-(hexadecyloxy)phenyl]methyl ester phosphonic acid
E - (Z)-9-octadecenamide
F - 2-(M)-chloroanilino)-5-methyl-trans-cinnamic acid
G - 2-(O)-fluoroanilino)-5-methyl-trans-cinnamic acid
ND = No data available

IV. Conclusion

The foregoing studies with Caco-cells and rats clearly indicate that pancreatic PLA$_2$ is pivotal in the intestinal absorption of lipids. The data also establishes that the compounds identified herein are useful in lowering cholesterol.

Data Supportinc the Utility of the Compounds Within the Scope of the Invention 1. Use of Fluorescence Method for Mass Screening of Pancreatic Phospholipase A$_2$ Inhibitors A sensitive fluorescence method was used to measure the activity of pancreatic phospholipase A$_2$ (PLA$_2$) in vitro. PLA$_2$ hydrolyzes the ester bond linking fatty acids to the sn-2 position in glycerophospholipids. Several types of PLA$_2$ exist, including those isolated from venoms, synovial fluid, platelets, immunoactive cell types and the pancreas. The pancreatic PLA$_2$ was the subject of this experiment because of its fundamental role in promoting lipid absorption in the intestine.

PLA$_2$ activity was detected by the loss of pyrene excimer fluorescence that occurs when (1-pyrenyl)-decanoic acid is hydrolysed from the sn-2 position of 1,2-bis-(1-pyrenedecanoyl)sn-glycero-3-phosphocholine ((P10)$_2$PC) by the action of PLA$_2$. The use of similar pyrene-labeled PC substrates to detect PLA$_2$ activity has been described previously (Radvanyi F., Jordan L., Russo-Marie F., Bon C., "A sensitive and continuous fluorometric assay for phospholipase A$_2$ using pyrene-labeled phospholipids in the presence of serum albumin." *Anal. Biochem.*, 177:103–109 (1989)). The full photophysical basis for the assay is described elsewhere (Birks J. B., "Photophysics of Aromatic Molecules," Wiley-Interscience, New York, pp. 301–371 (1970)).

In brief, pyrene excimers are formed by the complexation of one pyrene moiety in the ground-state with one pyrene moiety in the excited state to form an excited-state dimer (excimer) which fluoresces at longer wavelengths (475 nm emission maximum) than the wavelength range in which excited-state pyrene monomers fluoresce (370–400 nm). Excimer formation is dependent on the concentration of pyrene moieties. $(P10)_2PC$ emits excimer fluorescence almost exclusively due to the fixed juxtaposition of the pyrene chromophores. The substrate concentration is sufficiently dilute so that excimer formation between the products of $PLA_2$ action, namely lysoPY10PC and the (1-pyrenyl)decanoic acid, is insignificant.

In general, this assay scheme should have been apolicable to the study of any type of $PLA_2$. However, since pancreatic $PLA_2$ is unique from the other $PLA_2$'s in that it operates almost exclusively against micellized PC, the PC substrate in this assay was micellized with 1 mM deoxycholic acid. The PC component of the micelles consisted of 5 $\mu$M $(P10)_2PC$ substrate diluted with a 99-fold excess (495 $\mu$M) of 1-oleyl-2-palmityl phosphatidylcholine (OPPC). The OPPC was inert to $PLA_2$ hydrolysis because it contained ether-linked fatty alkyl chains in place of the ester-linked fatty acyl chains of normal PC. OPPC was included to 1) dilute the micellar $(P10)_2PC$ concentration thereby minimizing intermolecular excimer formation, and 2) preserve the integrity of the micelles against the action of $PLA_2$ since nonspecific micelle disruption could lead to nonlinear kinetics and fluorescence changes independent of lipolysis.

2. Materials and Methods 2.1 Reagents and Chemicals

Phospholipase $A_2$ (porcine pancreas), bovine serum albumin (BSA) (fraction V, essentially fatty acid-free) and sodium deoxycholate were obtained from Sigma Chemical Company, (St. Louis, Mo.). 1-Oleyl-2-palmityl-DL-phosphatidylcholine (OPPC) was ordered from Serdary Research Laboratories, Inc. (London, Ont., Canada). 1,2-Bis-(1-pyrenedecanoyl)-sn-glycero-3-phosphatidylcholine ($(P10)_2PC$) was obtained from Molecular Probes, Inc. (Eugene, Oreg.).

2.2 Stock Solutions

HEPES buffer (SHE) contained 150 mM NaCl, 20 mM HEPES (N-[2-hydroxyethyl] piperazine-N'-[2-ethanesulfonic acid]) and 1 mM EDTA (ethylenediamine tetraacetic acid) at pH 8.0.

1 M $CaCl_2$ in water 1 mM $(P10)_2PC$ in chloroform was prepared by adding 1 mL chloroform to a vial containing 1 mg of $(P10)_2PC$, as shipped by Molecular Probes. The actual concentration was determined spectrophotometrically by diluting 10 $\mu$L of the chloroform solution in 2 mL of ethanol. The absorbance spectrum of the ethanol solution was measured between 380 nm to 280 nm (Beckman DU-64). The height (ODU) of the 342 nm absorbance peak was multiplied by 200 and divided by $1.5 \times 10^5$ $M^{-1}cm^{-1}$ (extinction coefficient) to obtain the concentration of $(P10)_2PC$ in chloroform.

2 mM sodium deoxycholate in SHE was prepared by adding the appropriate amount of sodium deoxycholate to SHE and adjusting the pH 8.0 with 1N NaOH.

26.7 mM OPPC in chloroform (20 mg/mL) as shipped by Serdary Research Laboratories.

0.2% BSA (W/V) in SHE 2.3 Working Solutions

For every 10 mL of substrate solution 50 $\mu$L of 1 mM $(P10)_2PC$ and 185 $\mu$L of 26.7 mM OPPC were combined in a glass container and the chloroform was evaporated under a stream of $N_2$. Residual solvent was removed by 1 to 2 hours of vacuum. The dried lipids were dispersed in 10 mL of 2 mM sodium deoxycholate in SHE. Complete lipid dispersion was ensured by placement in a water bath sonicator. The final solution should be optically clear.

Enzyme solutions were prepared by diluting 3 $\mu$L of $PLA_2$, which is supplied as a suspension in 3.2 M ammonium sulfate by Sigma (ca. 5000 Units/mL, 6–7 mg/mL), in 20 mL of 0.2% BSA/SHE. 240 $\mu$L of 1 M $CaCl_2$ was added to obtain a final $[Ca^{++}]$ of 12 mM. The activity of each working $PLA_2$ solution was tested to ensure that 50% hydrolysis of the substrate occurred in approximately 60 minutes. Enzyme dilutions were adjusted accordingly.

2.4 Instrumentation

ICN/Labsystems Fluoroskan-II fluorescence microplate scanner equipped with a 340 nm bandpass filter (38% peak transmittance) (Ealing Electro-Optics, Holliston, Mass.) and Schott UG11 filter (2 mm thickness) (Schott Glass Technologies, Inc., Duryea, P.) in the excitation light path and a 480 nm bandpass filter (50% peak transmittance) (Corion Corp., Holliston, Mass.) in the emission light path.

2.5 Assay Methods

5 $\mu$L DMSO was added to wells A1, A12, B1, B12, C1, C12 of each 96-well master plate.

5 $\mu$L reference inhibitor was added to wells D1, E1 and F1.

Control wells were set up in positions A12, B12 and C12 by adding 50 $\mu$L 0.2% BSA in SHE.

50 $\mu$L enzyme working solution was added to all wells in columns 1 through 11.

Plate was covered, shaken, and allowed to stand for 5–10 minutes to allow equilibration of compounds with enzyme.

Plate was scanned in Fluoroskan-II to obtain background fluorescence readings.

50 $\mu$L substrate working solution was added to all wells in columns 1 through 12, shaken, and allowed to stand for 5 minutes.

Plate was scanned in Fluorskan to obtain initial fluorescence.

Plate was covered and allowed to stand (room temperature) for 60 minutes.

Scanned again to obtain fluorescence at 60 minutes reaction time.

3. Data Analysis

Location of reference wells in 96-well, X and Y masterplates. Z represents the wells containing $PLA_2$ and substrate without inhibitor. R represents the wells containing the reference inhibitor in addition to $PLA_2$ and substrate. X identifies the wells containing only substrate, without $PLA_2$.

|   | 1 | 2 | 3 | 4 | 5 | 6 | 7 | 8 | 9 | 10 | 11 | 12 |
|---|---|---|---|---|---|---|---|---|---|----|----|----|
| A | Z |   |   |   |   |   |   |   |   |    |    | X  |
| B | Z |   |   |   |   |   |   |   |   |    |    | X  |
| C | Z |   |   |   |   |   |   |   |   |    |    | X  |
| D | R |   |   |   |   |   |   |   |   |    |    |    |
| E | R |   |   |   |   |   |   |   |   |    |    |    |
| F | R |   |   |   |   |   |   |   |   |    |    |    |
| G |   |   |   |   |   |   |   |   |   |    |    |    |
| H |   |   |   |   |   |   |   |   |   |    |    |    |

The percent inhibition was calculated from the fluorescence values obtained for each well at 0 minutes and 60 minutes following substrate addition. Before this calculation was performed, the fluorescence values obtained at 60 minutes were corrected for detector drift over the 60-minute time period. The substrate fluorescences in the wells marked as X were used for this since they should be constant. This was accomplished by multiplying the fluorescence values obtained at 60 minutes by the ratio of X-well values at t=0 minutes over X-well values at 60 minutes (Equation 1).

$$F(\alpha, \beta)_{t=60} = f(\alpha, \beta)_{t=60} \times \frac{\sum X(\alpha = A, B, C; \beta = 12)_{t=0}}{\sum X(\alpha = A, B, C; \beta = 12)_{t=60}} \quad (1)$$

Here F ($\alpha,\beta$) is the corrected fluorescence for the well at row=$\alpha$ and column=$\beta$. The observed fluorescence is f ($\alpha,\beta$).

The change in fluorescence at each well position over a 60-minute time interval, relative to the corresponding change in fluorescence in the wells labeled Z was used to calculate the percent inhibition as follows:

$$\% I = 1 - \frac{F(\alpha, \beta)_{t=0} - F(\alpha, \beta)_{t=60}}{Z_{t=0} - Z_{t=60}} \quad (2)$$

Here Z represents the average fluorescence in the wells labeled as Z.

4. Results

Figure 12:
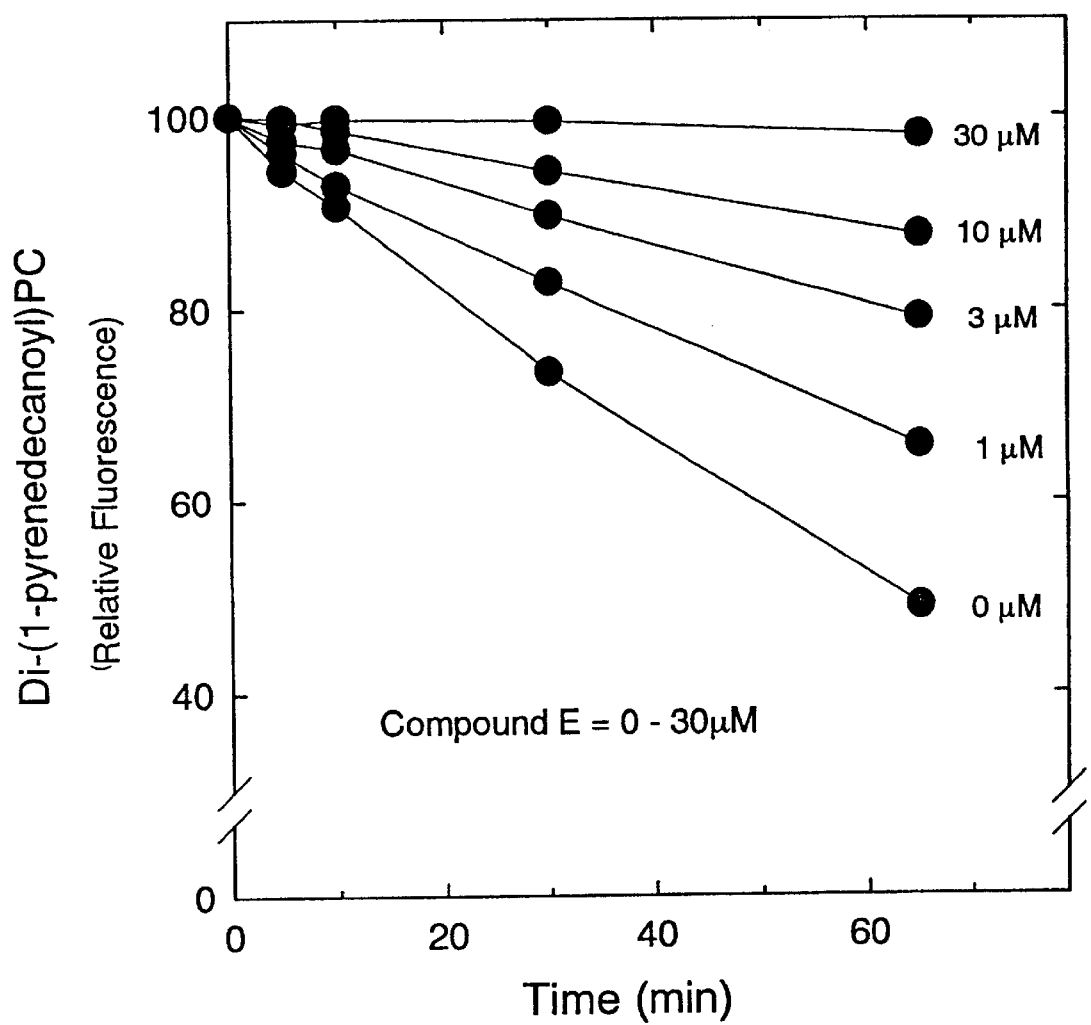
FIG. 12 shows the $PLA_2$ inhibitory activity of varying concentrations of (Z)-9-octadecen-amide, Compound E.

The utility of the assay for detection and characterization of PLA$_2$ inhibitors is demonstrated in FIG. 12 where (Z-9-octadecenamide, Compound E) inhibits 1,2-bis-(1-pyrenedecanoyl)-PC hydrolysis caused by PLA$_2$. Oleoylamide, the common name for Compound E, was first identified as a PLA$_2$ inhibitor by Jain and coworkers (Jain M. K., Ghomashchi F., Yu B-Z., et al., J. Med. Chem., 35:3584–3586 (1992)) who obtained an IC$_{50}$ of 0.1 $\mu$M in a "scooting-model" assay based on the use of methylphosphatidic acid as the substrate. Compound E yielded an IC$_{50}$ of 3 $\mu$M in the fluorescence assay (FIG. 12).

Figure 13:
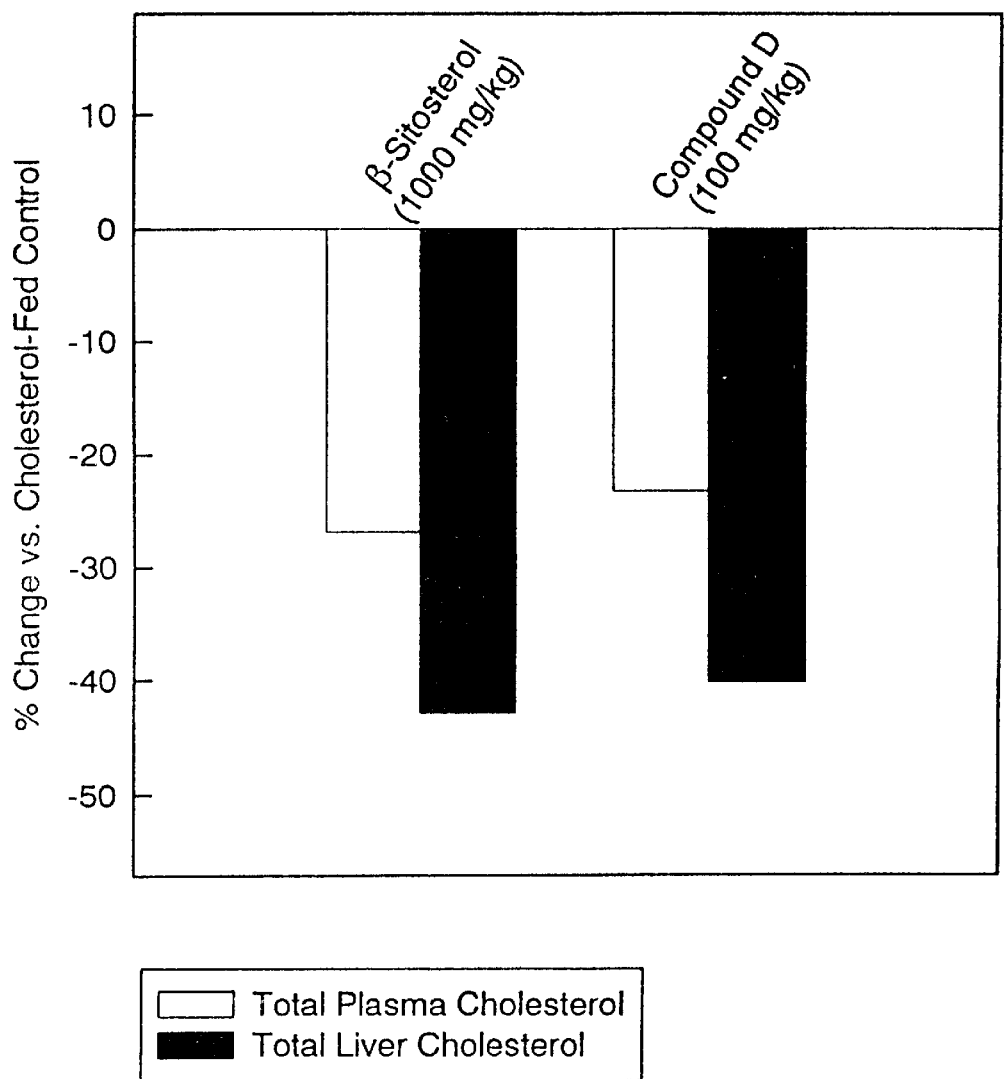
FIG. 13 shows that cholesterol absorption in hamsters is reduced by administering either β-sitosterol or Compound D.

Neomycin and β-sitosterol (Cytellin) have been used as cholesterol absorption inhibitors to treat hypercholesterolemic patients (Kesaniemi, et al., Serum cholesterol lowering by inhibition of cholesterol absorption, Atherosclerosis, VIII:791–794 (1989)). The mechanisms by which these agents inhibit intestinal cholesterol absorption are unknown. Relatively large doses must be administered (1.5–2 g/day neomycin, 3–50 g/day β-sitosterol) to achieve up to 25%; reductions in serum cholesterol levels. The advantages of PLA$_2$ inhibitors over these agents is that the mechanism of cholesterol absorption inhibition is known and sufficiently potent PLA$_2$ inhibitors could be administered in much smaller doses (potentially fewer side effects and better patient compliance) to achieve greater reductions in serum cholesterol levels. For example, in a cholesterol-fed hamster model, administration of 100 mg/kg of the phospholipase A$_2$ inhibitor methyl-[2-(hexadecyloxy)phenyl]methyl ester phosphonic acid (Compound D in FIG. 13) produced reductions in plasma and liver cholesterol levels nearly equivalent to those obtained with a ten-fold higher dose (i.e., 1000 mg/kg) of β-sitosterol. These data are graphically shown in FIG. 13. Pancreatic PLA$_2$ inhibitors represent a significant advancement over current agents, the use of which has already proven cholesterol absorption inhibitors to be a beneficial and effective therapy for hypercholesterolemia.

The maximum decrease in plasma cholesterol levels obtainable with cholesterol absorption inhibitors is not known. The experimental data for PLA$_2$ suggests that nonabsorbable PLA$_2$ inhibitors will have profound effects on cholesterol absorption. Nonabsorbable inhibitors would be preferred because: 1) they would be retained at the site of action, and 2) potential side-effect problems associated with systemically available drugs would be avoided.

Since intestinal cholesterol absorption is one unique component of the cholesterol turnover cycle in the body the potential exists for cholesterol absorption inhibitors to be used to augment the effects of other hypocholesterolemic agents directed at separate parts of the cholesterol metabolism pathway (e.g., HMG-CoA reductase inhibitors).

Use of PLA$_2$ Inhibitors to Block Triglyceride or Cholesteryl Ester Lipolysis

Results from in vitro experiments by Borgstrom and coworkers (Borgstrom B., "Importance of phospholipids, pancreatic phospholipase A$_2$, and fatty acid for the digestion of dietary fat." Gastroenterology, 78:954–962 (1980); Lindstrom M. B., Persson J., Thurn L., and Borgstrom B., "Effect of pancreatic phospholipase A$_2$ and gastric lipase on the action of pancreatic carboxyl ester lipase against lipid substrates in vitro." Biochem. Biophys. Acta, 1084:194–197 (1991)) suggest that intact lumenal PC interferes with more components of intestinal lipid uptake than just cholesterol absorption. They observed that in mixed lipid dispersions of PC containing triglyceride (TG) or cholesteryl ester (CE), pancreatic triglyceride lipase and carboxyl ester lipase were unable to hydrolyze their respective substrates unless phospholipase A$_2$ was added to the lipid mixture first to hydrolyze PC. These results suggest that lumenal PC may also block TG and CE lipolysis in the gut, and therefore, use of the PLA$_2$ inhibitors of the present invention may be used to treat diseases which result from TG and CE absorption.

I claim:

1. A method of treating atherosclerosis or coronary artery disease in a mammal suffering therefrom which comprises administering to said mammal an effective amount of a compound of the formula

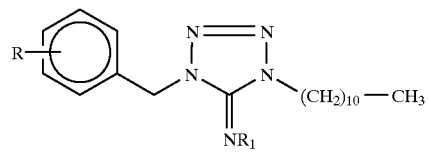

wherein R and R$_1$ are independently hydrogen, hydroxy, lower alkyl, halogen, trifluoromethyl, cyano, nitro, methylthio, lower alkenyl or lower alkynyl or a pharmaceutically acceptable salt thereof.

2. The method of claim 1 wherein R is a lower alkyl.

3. The method of claim 1 employing 1,4-dihydro-1-(phenylmethyl)-4-undecyl-5H-tetrazol-5-imine.

4. A method for blocking intestinal cholesterol absorption in an animal comprising administering to an animal in need of treatment a therapeutically effective amount of a pancreatic phospholipase A$_2$ inhibitor of the formula

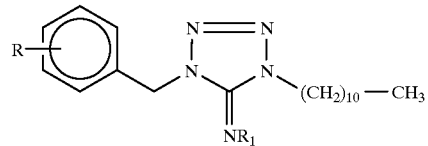

wherein R and R₁ are independently hydrogen, hydroxy, lower alkyl, halogen, trifluoromethyl, cyano, nitro, methylthio, lower alkenyl or lower alkynyl or a pharmaceutically acceptable salt thereof.

5. A method for reducing blood cholesterol levels in hypercholesterolemic subjects comprising administering to a subject in need of treatment a therapeutically effective amount of a pancreatic phospholipase A₂ inhibitor of the formula

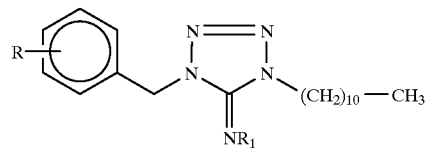

wherein R and R₁ are independently hydrogen, hydroxy, lower alkyl, halogen, trifluoromethyl, cyano, nitro, methylthio, lower alkenyl or lower alkynyl or a pharmaceutically acceptable salt thereof.

* * * * *